US012558010B2

(12) United States Patent
Devani

(10) Patent No.: US 12,558,010 B2
(45) Date of Patent: Feb. 24, 2026

(54) SYSTEMS AND METHODS FOR EVALUATING PUPILLARY RESPONSE

(71) Applicant: BioTrillion, Inc., San Francisco, CA (US)

(72) Inventor: Savan R. Devani, San Francisco, CA (US)

(73) Assignee: BioTrillion, Inc., San Francisco, CA (US)

( * ) Notice: Subject to any disclaimer, the term of this patent is extended or adjusted under 35 U.S.C. 154(b) by 981 days.

(21) Appl. No.: 17/636,298

(22) PCT Filed: Aug. 19, 2020

(86) PCT No.: PCT/US2020/046992
§ 371 (c)(1),
(2) Date: Feb. 17, 2022

(87) PCT Pub. No.: WO2021/034931
PCT Pub. Date: Feb. 25, 2021

(65) Prior Publication Data
US 2022/0287607 A1 Sep. 15, 2022

Related U.S. Application Data

(60) Provisional application No. 62/889,366, filed on Aug. 20, 2019, provisional application No. 62/889,409, filed on Aug. 20, 2019.

(51) Int. Cl.
*A61B 5/16* (2006.01)
*A61B 3/00* (2006.01)
(Continued)

(52) U.S. Cl.
CPC ............ *A61B 5/163* (2017.08); *A61B 3/0025* (2013.01); *A61B 3/112* (2013.01); *A61B 3/14* (2013.01);
(Continued)

(58) Field of Classification Search
CPC ....... A61B 5/163; A61B 3/112; A61B 3/0025; A61B 3/14; A61B 5/6898; G06T 7/0012;
(Continued)

(56) References Cited

U.S. PATENT DOCUMENTS

2006/0077348 A1    4/2006  Gorin
2006/0147094 A1    7/2006  Yoo
(Continued)

FOREIGN PATENT DOCUMENTS

JP    2002253509 A    9/2002
JP    2007531579 A    11/2007
(Continued)

OTHER PUBLICATIONS

International Search Report in International Patent Application No. PCT/US2020/046992, mailed Nov. 9, 2020 (2 pages).
(Continued)

*Primary Examiner* — Eric F Winakur
*Assistant Examiner* — Sienna C Pyle
(74) *Attorney, Agent, or Firm* — Nixon Peabody LLP

(57) ABSTRACT

The present disclosure is directed to systems and methods for measuring pupillary responses to visible light stimuli. An exemplary system provides a display and a camera on the same side of a device; the display provides a visible light stimulus to illuminate a user's face and cause a pupillary reflex. A visible light or infrared camera thereafter receives image data of the pupillary light reflex. In some examples, an ambient light sensor and infrared measurement systems allow for performing pupillary light reflex assessments in low lighting conditions.

18 Claims, 10 Drawing Sheets

(51) Int. Cl.

| | | |
|---|---|---|
| *A61B 3/11* | (2006.01) | |
| *A61B 3/14* | (2006.01) | |
| *A61B 5/00* | (2006.01) | |
| *G06T 7/00* | (2017.01) | |

(52) U.S. Cl.
CPC .......... *A61B 5/6898* (2013.01); *G06T 7/0012* (2013.01); *G06T 2207/10048* (2013.01); *G06T 2207/30041* (2013.01)

(58) Field of Classification Search
CPC .......... G06T 2207/10048; G06T 2207/10024; G16H 50/20; G16H 30/40
See application file for complete search history.

(56) References Cited

U.S. PATENT DOCUMENTS

| | | | | |
|---|---|---|---|---|
| 2008/0117384 | A1* | 5/2008 | Inakagata | ............... A61B 3/111 351/243 |
| 2010/0156865 | A1 | 6/2010 | Kreek | |
| 2012/0262069 | A1 | 10/2012 | Reed | |
| 2012/0268715 | A1 | 10/2012 | Stark | |
| 2015/0190048 | A1* | 7/2015 | Huang | ................. A61B 3/0033 351/239 |
| 2016/0262611 | A1* | 9/2016 | Rotenstreich | ........ A61B 3/0025 |
| 2017/0079527 | A1* | 3/2017 | Daneshi Kohan | ... A61B 3/0025 |
| 2017/0311799 | A1 | 11/2017 | Holt et al. | |
| 2017/0347878 | A1 | 12/2017 | Milea et al. | |
| 2018/0078216 | A1* | 3/2018 | Baker | ................. A61B 3/0025 |

FOREIGN PATENT DOCUMENTS

| | | |
|---|---|---|
| JP | 2016537152 A | 12/2016 |
| WO | 2018213245 A1 | 11/2018 |
| WO | 2019023547 A1 | 1/2019 |

OTHER PUBLICATIONS

Written Opinion of the International Searching Authority in International Patent Application No. PCT/US2020/046992, mailed Nov. 9, 2020 (9 pages).
Japanese Patent Office Action in Application No. 2022-513562 with English Translation, mailed Feb. 18, 2025 (5 pages).

* cited by examiner

300

1112

1110

1122

1120

1202

1202

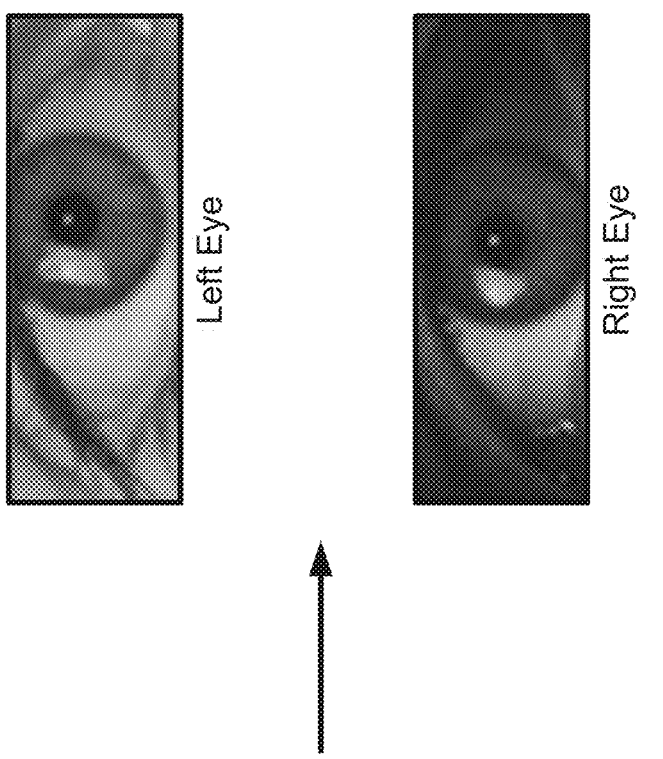
Left Eye
Right Eye
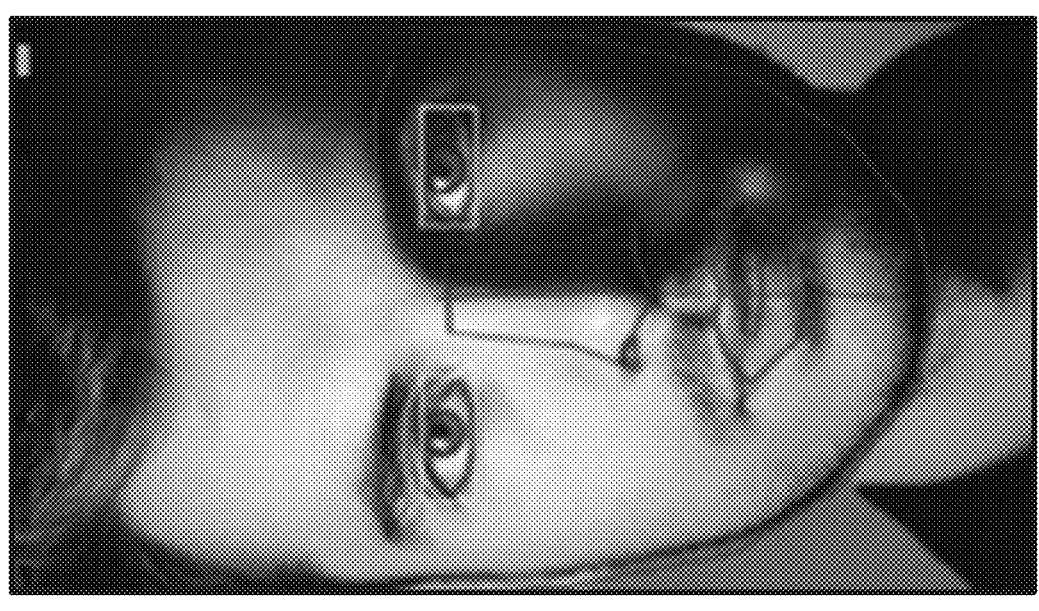
FIG. 9

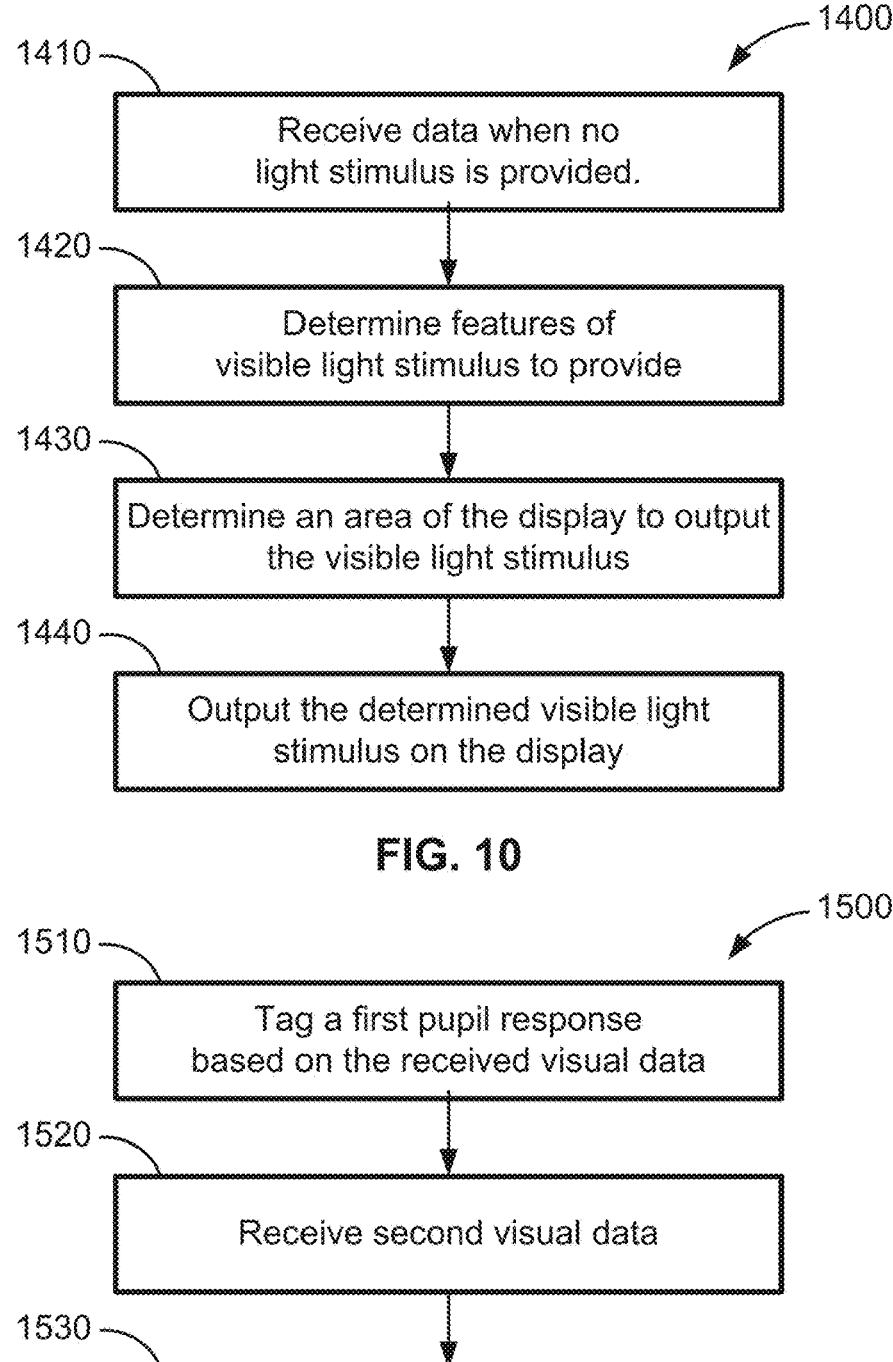

1400

1410 — Receive data when no
light stimulus is provided.

1420 — Determine features of
visible light stimulus to provide

1430 — Determine an area of the display to output
the visible light stimulus

1440 — Output the determined visible light
stimulus on the display

1510 — Tag a first pupil response
based on the received visual data

1520 — Receive second visual data

1530 — Determine a change in lighting conditions
based on the received visual data 1540 — Tag a second pupil response

FIG. 11

1610 — Emit visible light stimulus

1620 — Emit non-visible radation

1630 — Detect non-visible radiation corresponding to an eye of a user

1640 — Process the visual data to identify a pupil feature

1650 — Determine a health status based on the pupil feature

SYSTEMS AND METHODS FOR EVALUATING PUPILLARY RESPONSE

CROSS-REFERENCE TO RELATED APPLICATIONS

This application is a U.S. National Stage of International Application No. PCT/US2020/046992, filed Aug. 19, 2020 which claims priority to and the benefit of U.S. Provisional Patent Application No. 62/889,409, filed Aug. 20, 2019, titled "SYSTEMS AND METHODS FOR EVALUATING PUPILLARY RESPONSE," and U.S. Provisional Patent Application No. 62/889,366, filed Aug. 20, 2019, titled "SYSTEMS AND METHODS FOR EVALUATING PUPILLARY RESPONSE," each of which are incorporated herein by reference in their entirety entireties.

FIELD

The present disclosure relates to systems and methods for measuring and analyzing pupillary response.

BACKGROUND

Pupils constrict and dilate in response to various external (e.g., light) and internal (e.g., cognitive/emotional) stimuli. Pupil responses are evaluated for many aspects of physiologic and behavioral health; conventional measurement methods use a pupilometer. Pupilometers are expensive, costing as much as $4,500, are mainly used in medical settings, and must be used by a trained clinician. Other conventional measurements use a penlight exam, where a clinician directs a penlight towards the patient's eyes and observes the pupils' responses.

SUMMARY

Conventional measurement methods have substantial drawbacks, including a lack of standardization, a need for deliberate training, variances between different measuring-operators over time, and poor inter-observer reliability or reproducibility. Penlight exams are conventionally used in emergency first aid situations, where rapid, qualitatively-crude assessments, accessibility, and convenience are prioritized over precision. Furthermore, even semi-automated conventional methods for measuring pupillary response require new or external physical hardware to ensure any or all of (1) proper ambient lighting conditions, (2) proper alignment of face/eyes guided by the front of mobile device display, (3) sufficient stimulus for pupillary response, and/or (4) adequate processing power for performing external image processing/feature extraction.

In addition to the disadvantages of conventional pupillary measurement systems, these devices use visible light as the stimulus source followed by visible light as the illumination source for image capture; in some examples, use of the visible light spectrum to measure the pupil post the stimulation phase may catalyze unintentional pupillary responses, akin to the "observer effect" in physics where the mere observation of a phenomenon inevitably changes that phenomenon—often the result of instruments that, by necessity, alter the state of what they measure in some manner. Furthermore, conventional systems need to (1) provide enough light stimulus to achieve the high levels of contrast required for pupil-iris segmentation with (2) ensure moderately—to well-lit lighting conditions to illuminate the face for adequate image capture.

Lastly, these conventional methods typically may only catch signs of disease occurrence after the disease is acutely symptomatic or progressively developed, which may be beyond the most treatable phase of the disease.

The various examples of the present disclosure are directed towards a system for evaluating pupillary light reflex. The system may include a mobile device, a camera, a display, a processor, and a memory. The mobile device includes a front side and a back side; a camera and a display are located on the front side of the mobile device and an additional camera may be located on the back side of the device. The memory includes a plurality of code sections executable by the processor. The plurality of code sections include a series of instructions. The instructions may provide for emitting at least one visible light stimulus by a display. The instructions then provide for receiving, from the camera, image data corresponding to at least one eye of a user. The instructions then provide for processing the image data to identify at least one pupil feature. The instructions then provide for determining a health status based on the at least one pupil feature.

In some examples, the instructions further provide for outputting the health status at the display.

In some examples, processing the image data to identify at least one pupil feature includes preprocessing the received image data.

In some examples, identifying at least one pupil feature based on the received image data includes segmenting the received image data to determine first data portions corresponding to a pupil of the eye and second data portions corresponding to an iris of the eye.

In some examples, the at least one pupil feature includes at least one of: pupil response latency, constriction latency, maximum constriction velocity, average constriction velocity, minimum pupil diameter, dilation velocity, 75% recovery time, average pupil diameter, maximum pupil diameter, constriction amplitude, constriction percentage, pupil escape, baseline pupil amplitude, post-illumination pupil response, and any combination thereof.

In some examples, determining a health status based on the at least one pupil feature further includes: (1) determining a difference between each of the at least one pupil feature and a corresponding healthy pupil measurement, and (2) determining the health status based on the determined difference for each of the at least one pupil feature and the at least one pupil feature. For example, the corresponding healthy pupil measurement is retrieved, by the processor, from an external measurement database In some examples, emitting at least one visible light stimulus by the display includes (1) receiving first image data of the eye when no light stimulus is provided by the display, (2) determining an amount of luminous flux to provide based on the first image data, (3) determining an area of the display to output the determined amount of luminous flux, and (4) outputting the determined amount of luminous flux on the determined area of the display. In some examples, second image data of the eye is received after outputting the luminous flux. In some examples, the output luminous flux is adjusted based on the second image data.

In some examples, the instructions further provide for tagging a first pupil response based on the received image data. Second image data is then received. The instructions then provide for determining a change in lighting conditions based on the second image data. A second pupil response is then tagged.

The present disclosure further provides an exemplary method for evaluating pupillary light reflex. The method provides for emitting at least one visible light stimulus by the display. The method then provides for receiving, from the camera, image data corresponding to an eye of a user. The method then provides for processing the image data to identify at least one pupil feature. The method then provides for determining a health status based on the at least one pupil feature. Additional examples of this method are as described above with respect to the exemplary system.

The present disclosure further provides for a non-transitory machine-readable medium comprising machine-executable code. When executed by at least one machine, the machine-executable code causes the machine to emit at least one visible light stimulus by the display. The code then provides for receiving, from the camera, image data corresponding to an eye of a user. The code then provides for processing the image data to identify at least one pupil feature. The code then provides for determining a health status based on the at least one pupil feature. Additional examples of this code are as described above with respect to the exemplary system.

In another exemplary embodiment, the present disclosure provides another system for evaluating pupillary light reflex. The system includes a hardware device, a camera, a display, a processor, and a memory. The hardware device includes a front side and a back side; the camera and the display are located on the front side of the hardware device. The memory includes a plurality of code sections executable by the processor. The code sections include instructions for emitting at least one visual stimulus by the display. The instructions further provide for emitting at least one non-visible light by an infrared emitting device. The instructions then provide for receiving, from the camera or an infrared detector, image data corresponding to an eye of a user. In some examples, the infrared detector will receive ambient infrared light and an infrared emitting device will not be necessary. The instructions then provide for processing the image data to identify at least one pupil feature. The instructions then provide for determining a health status based on the at least one pupil feature.

In some examples, the non-visible light emission with a wavelength between 700 nm and 1000 nm. In some examples, the non-visible light emission includes far infrared wavelengths.

In some examples, the camera is an infrared camera.

In some examples, identifying at least one pupil feature based on the received image data includes (1) determining image contrast of the received image data, (2) determining that the image contrast is lower than a threshold contrast level, and (3) outputting, on the display, a prompt for the user to provide second image data at a more dimly lit location. For example, the at least one pupil feature is determined based on the second image data.

In some examples, the at least one pupil feature includes at least one of: pupil response latency, constriction latency, maximum constriction velocity, average constriction velocity, minimum pupil diameter, dilation velocity, 75% recovery time, average pupil diameter, maximum pupil diameter, constriction amplitude, constriction percentage, pupil escape, baseline pupil amplitude, post-illumination pupil response, and any combination thereof.

In some examples, identifying at least one pupil feature based on the received image data further includes segmenting the received image data to determine data portions corresponding to a pupil of the eye and data portions corresponding to an iris of the eye.

In some examples, the hardware device is a headset.

In some examples, the hardware device is a smartphone.

The above summary is not intended to represent each embodiment or every aspect of the present disclosure. Rather, the foregoing summary merely provides an example of some of the novel aspects and features set forth herein. The above features and advantages, and other features and advantages of the present disclosure, will be readily apparent from the following detailed description of representative embodiments and modes for carrying out the present invention, when taken in connection with the accompanying drawings and the appended claims.

BRIEF DESCRIPTION OF THE DRAWINGS

The accompanying drawings exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

FIG. 9 shows exemplary eye bounding detection, according to an embodiment of the present disclosure.

FIG. 10 shows an exemplary method for determining luminous flux, according to an embodiment of the present disclosure.

FIG. 11 shows an exemplary methodology for identifying a second pupillary response, according to an embodiment of the present disclosure.

DETAILED DESCRIPTION

Figure 1:
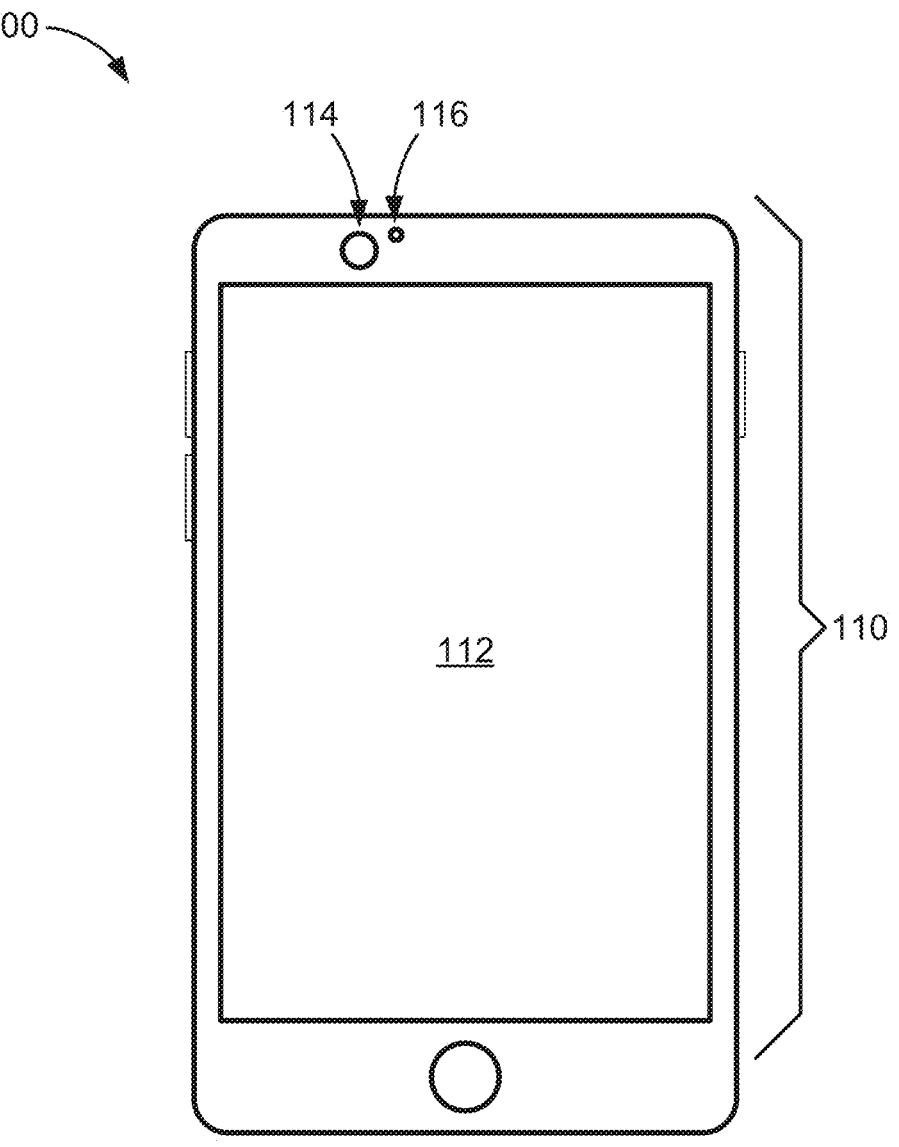
FIG. 1 shows an exemplary system 100, according to an embodiment of the present disclosure.

The present invention is described with reference to the attached figures, where like reference numerals are used throughout the figures to designate similar or equivalent elements. The figures are not drawn to scale, and are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details, or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

Overview

The present disclosure is directed to systems and methods for measuring pupillary responses. In some examples, the disclosed technology uses the display of a mobile device to deliver the light stimulus to trigger the pupillary light response, which may then be recorded by a visible light or infrared camera located on the same side of the mobile device as the display. Additionally, the technology may record the pupillary light reflex in low light conditions so that the display of a mobile device may deliver sufficient light stimulus (relative to the ambient light) to trigger the pupillary light reflex of a user. Accordingly, an infrared detector (and in some cases an infrared emitter) may be utilized to record the images of the eye and determine the user's pupillary light reflex when the system is used in low lighting conditions.

This is advantageous, because the system may allow a mobile device to record a pupillary light reflex using a front facing camera and a display in low/dark lighting conditions, so that the user does not have to use a box or other device to block out ambient light, and the infrared system used to record the pupillary reflex will not trigger an additional light reflex which may confound the measurement.

In one example, when a user unlocks their phone in a room with low ambient lighting (e.g. at night) using a facial identification software, the pupillary light reflex test application may be initiated by flashing the display at a threshold brightness to deliver a visible light stimulus while unlocking the phone. The system may then record the pupillary light reflex while the user unlocks the phone as disclosed further herein.

In some examples, the system provides a display and a camera on the same side of a device; the display may provide a visible light stimulus to stimulate a user's eye and catalyze a pupillary reflex. The camera simultaneously receives image data of the pupillary reflex. Therefore, an exemplary device according to the present disclosure can provide a more scalable (accessible, affordable, and convenient) and more accurate (objective and quantitative) system than current systems and methods, which can be used by the user with or without a health professional or non-health professional.

For instance, in prior systems, a backward facing camera and flash on the back of a smartphone has been attempted to be used to measure pupillary light reflex, but a user would be unable to self-measure their PLR using that system, and thus would require dependence on a second measurement-operator and potential longitudinal measurement inconsistencies stemming from multiple measurement-operators. However, prior systems have not attempted to use the front facing camera because the front of mobile devices may not include a flash and therefore a light stimulus could not be generated to initial the pupillary light reflex. Furthermore, typical flashes are monochromatic and have a limited range of spectral frequencies and intensities of emission. Accordingly, the inventors discovered the display on the front of a smart phone or similar device could be utilized to provide the light stimulus, based on the methods and features described herein. In some examples, the display may deliver white, green, blue, or red light, depending the health status the system is determining.

The disclosed technology is also advantageous, because using a front-facing camera and display allows the users themselves to more accurately, scalably, and frequently perform the pupillary light reflex measurement using a smart phone or other related device. For instance, the user can line up the eyes correctly because the display is also on the front side of the device, without help from another individual. This allows the user to frequently perform the measurement because they do not require another caregiver to perform the measurement. Thus, the system allows the user to collect data more frequently and obtain longitudinal data on their health conditions (whereas single measurements may not be sufficient to identify certain conditions where longitudinal data is required, including for establishing baselines and deviations from baselines). Additionally, utilizing the display to provide the stimulus will allow the system to have more precise control and variability of the stimulus given the range of intensities and colors that may be displayed.

Finally, in some embodiments that utilize infrared detection, this system may be particularly advantageous because the infrared detection will allow a sufficient pupillary response to be generated by the eye, because measurement light will not trigger a secondary response of the pupils—which is important because the display has a lower maximum intensity than a rear facing flash, and thus a secondary response may prohibit the ability to record a sufficient pupillary light reflex. In some examples, the disclosed system includes a smartphone or other handheld computing device. Such a system allows frequent and accurate data collection, which can provide important quantitative data on user health. In some examples, as discussed further herein, the present disclosure provides for collection of longitudinal health data, which can be used to create baseline pupillary metric measurements for a user. Therefore, the present disclosure provides measurements pre-diagnosis, pre-trauma, and/or pre-disease, which can be used to monitor disease and/or trauma progression and/or establish an individualized longitudinal healthy baseline.

In some examples, the visible light stimulus generates sufficient photonic energy to catalyze a full pupillary reflex. Exemplary methods further include collecting data before the light intensity threshold is reached, and determining pupillary metrics as a function of other factors that affect pupillary response. Use of a front-facing display and front-facing camera further allows the disclosed system to control and monitor the ambient lighting conditions during image capture to ensure that a secondary accidental pupil response is not initiated when measuring the first, intentional pupil response. In some examples, an exemplary method detects ambient light levels to account for an effect that the ambient light levels had on the detected pupillary metrics, determine whether to use infrared or visible light based camera detection, and/or determine whether the room has low enough lighting for the display to deliver sufficient visible light stimulus to trigger a pupillary light reflex as described further herein. In some examples, the data collected before the light intensity threshold is reached provides baseline values for a user's pupillary metrics.

Some examples of the present disclosure further provide for using a visible light stimulus to illuminate the face and then using a non-visible emission (e.g. infrared radiation) for image capture (for instance, from ambient source or from an infrared emitter). Use of the non-visible emission avoids unintentionally triggering the pupillary light reflex which would confound the data. Additionally, due to the high level of contrast required between the light stimulus intensity and ambient lighting conditions in order to catalyze pupillary light reflex, performing an assessment in low ambient light conditions may be beneficial in some examples. However, in low ambient light conditions, the darkness of the room may interfere with the ability to capture a high-quality eye image necessary for evaluating a pupillary light reflex. For example, there is often minimal contrast between the pupil and iris components, particularly in an individual with higher pigmented, or darker irises. Distinguishing between these two features is critical to properly segment and measure the features for extraction and metric computation. Accordingly, utilization of an infrared camera system or other infrared hardware may allow for the disclosed technology to record and analyze high-resolution pupil images for effective feature segmentation when assessments are performed in low ambient light conditions.

Systems for Measuring Pupil Metrics

FIG. 1 provides an exemplary system 100, according to an embodiment of the present disclosure. In some examples, system 100 may include a smart phone, a smart watch, a tablet, a computing device, head gear, head set, virtual reality device, augmented reality device, or any other device capable of receiving and interpreting a physical signal. System 100 may include a housing 110, a display 112, a camera 114 and a flash, and a sensor 116. FIG. 1 shows a front side of the system 100.

The housing 110 provides a case for the display 112, the camera 114, and the sensor 116. The housing 110 further includes any computing components (not shown) of the system 100, including, for example, a processor, a memory, a wireless communication element, and any other elements as readily contemplated by one skilled in the art. The computing components further include any software configured to complete any of the processes discussed further herein.

The display 112 is, for example, the screen of a smartphone, a smart watch, an optical headset, or any other device. In some examples, the display 112 is an LCD screen, an OLED screen, an LED screen, touchscreen, or any other type of electronic display/interface, as known in the art, which shows images, text, or other types of graphical display. For example, the screen provides a plurality of light-emitting diodes or other means for generating a plurality of pixels. In some examples, the display is a screen of a virtual reality head set or smart glasses.

The display 112 is configured to emit visual light. In some examples, the display 112 emits light on a portion of a surface area of the display 112; in other examples, the display 112 emits light on all of a surface area of the display 112. The light emitted by the display 112 can be controlled to automatically emit light, and increase or decrease the visible light stimulus. In some examples, the display 112 shows image data captured by the camera 114.

The camera 114 receives image data of a field of view in front of the camera 114. In some examples, the camera 114 receives photographic and/or video data. In some examples, the camera 114 receives continuous photographic data (e.g., at intervals of seconds, milliseconds, or microseconds). In some examples, the camera 114 is a visual light camera. In some examples, the camera 114 is an infrared camera and includes an infrared light emitter. In some examples, the camera 114 automatically initiates image data capture based on detecting certain stimulus (for example, a face of a user, an eye of a user, a pupil of a user, and/or an iris of a user).

The camera 114 may also include an LED flash, xenon flash, or other suitable flash. In some examples, a flash may be on the front and/or back side of the system 100. The flash may be configured to emit a high intensity, short burst of white light, in some examples, in order to trigger a user's PLR.

The sensor(s) 116 may include, for example, a light sensor, an ambient light sensor, and/or an infrared sensor. In some examples, the sensor 116 is communicatively coupled to the camera 114 and is configured to initiate and/or terminate image data capture by the camera 114. The sensors 116 may be placed in various appropriate positions depending on the type of sensors utilized. As shown, the sensor 116 is on the same side of the system 100 as the camera 114. In some examples, the sensor 116 is placed proximally close to the camera 114. A light sensor may be any suitable light sensor capable of sensing the ambient light and output Irradiance/Illuminance in lux or W/m². For instance, a silicon based photosensor may be utilized to measure the lux incident on the mobile device.

Figure 2:
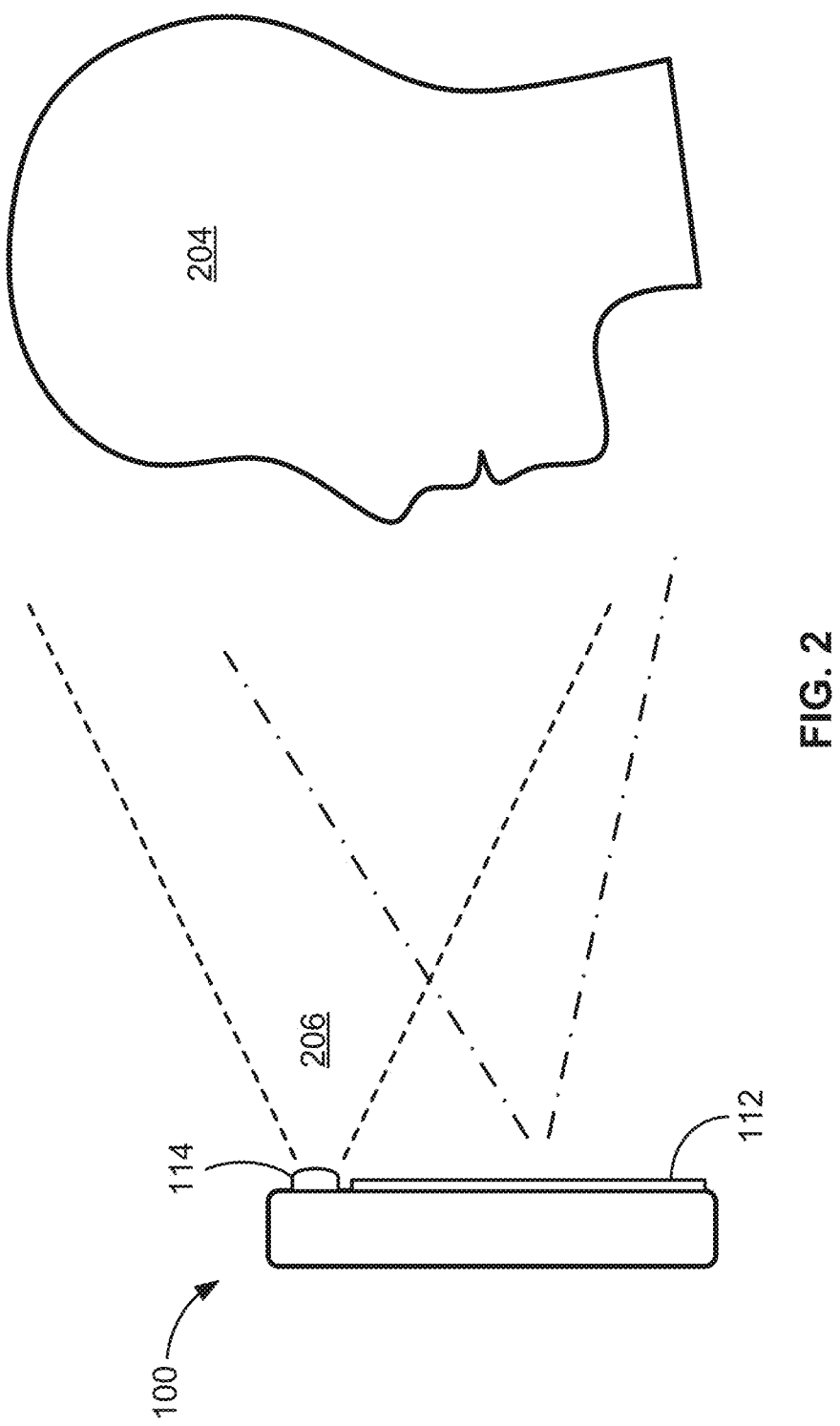
FIG. 2 shows an exemplary system 200 for measuring pupillary response, according to an embodiment of the present disclosure.

FIG. 2 shows an exemplary system 200 configured to receive image data of a user's face, according to an embodiment of the present disclosure. System 200 includes system 100, camera 114, a user's eye 202, a user's head 204, and a camera field of view 206. System 100 and camera 114 can be as discussed above with respect to FIG. 1. FIG. 2 shows that system 100 can be positioned such that the camera 114 faces a user 204. For example, the eye 202 of a user 204 can be with in the field of view of the camera 206. Various embodiments of the present disclosure can be performed when a user 204 positions system 100 in front of his face.

Methods for Analyzing Pupillary Light Reflex

Pupillary Light Reflex (PLR) describes the constriction and subsequent dilation of the pupil in response to light, which can serve as an important metric of autonomic nervous system function. The measurement of PLR can be used as an indicator of abnormalities with various nervous system pathways in the neurological system (and potentially other systems) and subsequently for detection of developing disease purposes. For example, alcoholism, mental health disorders such as seasonal affective disorders, schizophrenia and generalized anxiety disorder, Alzheimer's and Parkinson's diseases, autism spectrum disorders, as well as glaucoma and autonomic neuropathies associated with diabetes may result in anomalies in PLR.

The methodology described below describes one such measure of one component of the PLR, performed via the use of a smartphone or analogous device. In some embodiments, the smartphone may not only capture the phenotypic data for the PLR measurement, but also process the data locally and in real-time. Thus, the user's privacy may be better preserved and the time taken for the measurement may be reduced. The method and system may also allow for the calculation of dynamically changing diameter of pupil. The method and system may generate a more robust baseline upon which to detect real-time detect statistical deviations. Such deviations may be a sign of an anomaly in the physiologic system from which the measure is causally connected.

Figure 3:
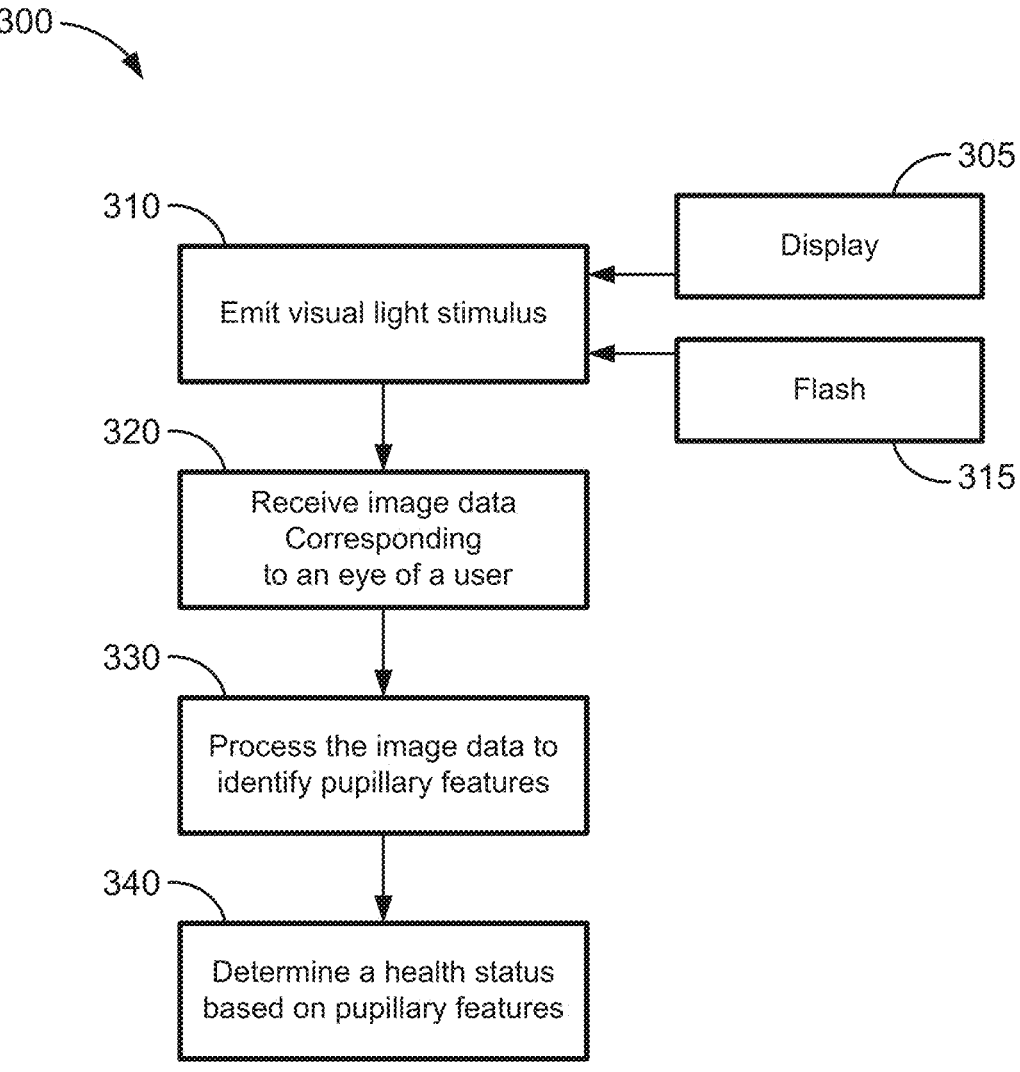
FIG. 3 shows an exemplary methodology 300 for identifying and analyzing pupil features, according to an embodiment of the present disclosure.

FIG. 3 shows an exemplary methodology 300 that can be performed according to the various embodiments of the present disclosure. Methodology 300 can be performed on systems 100 and 200 as discussed with respect to FIGS. 1 and 2. In some examples, methodology 300 is performed in a room with low ambient lighting, a room with natural light, or any other setting. For instance, a room with low ambient light may be a room with measured light using a light sensor that registers less than 150, 100, 90, 80, 70, 60, 50, 40, 30, 20, 10 4, 1, or 0.5 lux, or readings in-between. In some examples, methodology 300 is performed repeatedly, including, for example, performed at night or before bedtime by a user when external variables such as light are at a minimum and controllable.

In some example, methodology 300 begins at 310 by emitting a visible light stimulus by a display 305 or a flash 315 (e.g., display 112 or sensor 116 of FIG. 1). The emitted visible light stimulus, for example, causes pupil constriction. In some examples, the pupil constriction increases as a contrast increases between the visible light stimulus and an ambient light level. The features of the visible light stimulus provided can be as determined by methodology 1400 of FIG. 4, discussed further below.

In some examples of 310, the visible light stimulus is automatically emitted when a camera (e.g., camera 114 of system 100 of FIG. 1) or infrared detection systems detects that a user's face (e.g., user 204 of FIG. 2) is at an appropriate spatial distance and/or the ambient lighting conditions are appropriate for the type of visible light stimulus delivery device (e.g. display or flash). In some examples, the display first emits a notification that there will be imminent visible light stimulus.

Figure 8:
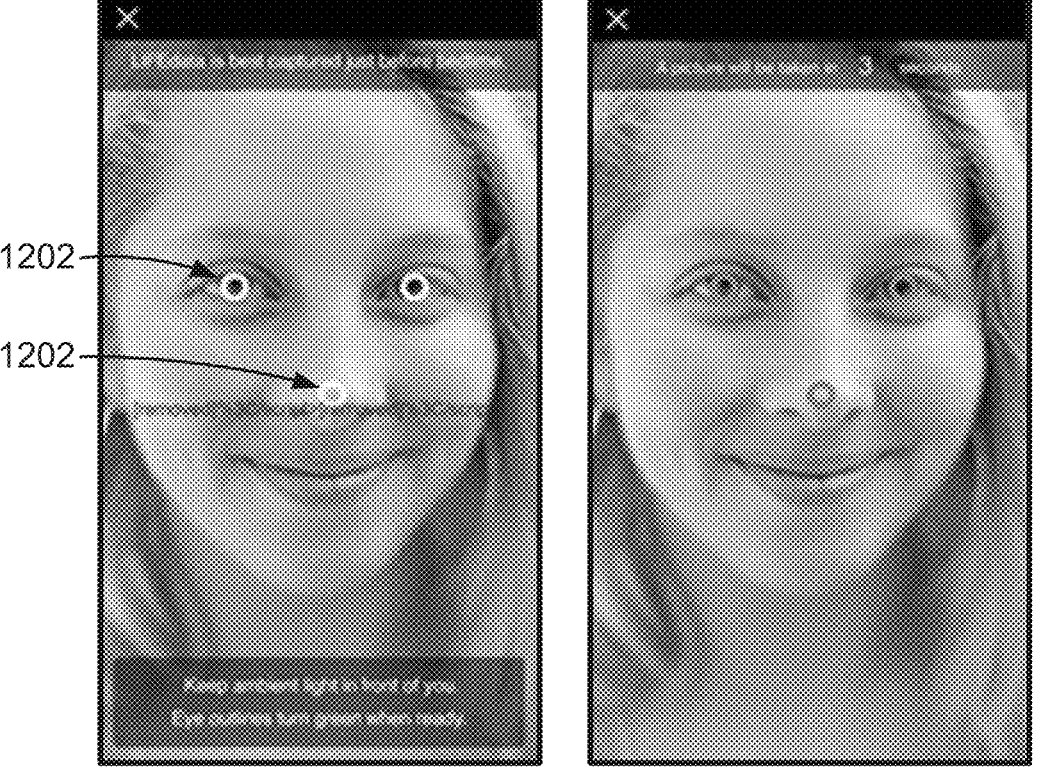
FIG. 8 shows an exemplary software application implementation which automatically detects proper lighting and spatial orientation, according to an embodiment of the present disclosure.

As shown in FIG. 8, for example, the display may show real-time captured image data of the user's face and provide a visual graphic that a user's features are properly detected. For example, circles 1202 can be placed on the user's eyes or nose. Turning briefly to FIG. 9, the display shows exemplary graphical user interface that include bounding boxes for the user's eyes, mouth, and nose.

Referring back to FIG. 3, in some examples, 310 provides for first detecting a pupil. If the pupil is not detected, the user is notified that the setting does not meet the criteria for methodology 300.

Methodology 300 then provides for receiving image data corresponding to an eye of a user at 320. Exemplary image data includes video, photographic, or infrared image data. In some examples, the image data is collected (e.g., collected by camera 114 of FIG. 1) over a period of time. In some examples, a video is recorded between 30-60 frames/sec, or at a higher frame rate. In some examples of 320, a set of still images are produced by a camera and/or infrared image capturing system. In some examples of 320, the image data is captured as a gray-scale video/image set, or is converted to grayscale after being received.

Processing Image Data to Identify Pupillary Features

Methodology 300 then proceeds to process the image data to identify pupillary features, at 330. In some examples of 330, the received image data is first pre-processed to clean the data. Exemplary types of data pre-processing are discussed further below. In a brief exemplary protocol for pre-processing data, the image data of 320 is cropped and filtered to obtain a region of image. For example, the image is filtered based on set thresholds for brightness, color, and saturation. The image data is then converted to gray scale to improve contrast between a pupil and an iris, and the pupil-iris boundary is demarcated. In some examples of 330, shape analysis is performed to filter the image data based on a pre-selected circularity threshold. For example, the pixels are scanned for contour and convex shapes to perform the shape analysis. In some examples of 330, a baseline image is compared to the received image data of 320 to aid in pre-processing.

In some examples, machine learning methods are used to identify the pupillary features, including deep learning methods. Methods may include other image processing and feature identification methods known in the art.

In some examples, 330 further provides for determining a surface area of pupil and iris regions, as detected in the image data. For example, imaging analysis software algorithms determine pupil size parameters across a series of recorded images by evaluating the elapsed time between each image to determine the rate at which the pupil size changes over time.

In some examples, identification information is optionally removed from the sensor data at 330. Stated differently, the most relevant key phenotypic features of interest may be extracted from the raw image data. Exemplary features include: pupil velocity (e.g. magnitude and direction), sclera color, a measure of tissue inflammation, and/or other characteristics. These features can be represented as scalar numbers after extracting relevant metrics from the underlying raw data. The image of the user that may be identifiable is not utilized.

In some examples of 330, the features include: (1) pupil response latency, which includes the time taken for a pupil to respond to a light stimulus measured, for example, in milliseconds; (2) maximum diameter, which is the maximum pupil diameter observed; (3) maximum constriction velocity (MCV), which is the maximum velocity observed over the constriction period; (4) average constriction velocity (ACV), which is the average velocity observed over the total constriction period; (5) minimum pupil diameter, which is the minimum diameter observed; (6) dilation velocity, which is the average velocity observed over the total dilation period; (7) 75% recovery time, which is the time for the pupil to reach 75% of its initial diameter value; (8) average diameter, which is an average of all diameter measurements taken in a time series; (9) pupil escape; (10) baseline pupil amplitude; (11) post-illumination pupil response; (12) maximum pupil diameter; (13) any other pupillary response measurements, as known in the art; and (14) any combination thereof. In some examples of 330, similar metrics are determined of the iris.

For example, constriction latency is measured as constriction ($t_{flash}$)–constriction ($t_{initial}$). For example, constriction velocity is a measure of the rate at which the pupil constricts in millimeters/second. For example, constriction amplitude is measured as (Diameter$_{max}$ prior to light exposure)–(Diameter$_{min}$ following light exposure). For example, constriction percentage is measured by taking the constriction amplitude as a percentage of Diameter$_{max}$. For example, dilation velocity is a measure of the rate at which the pupil dilates in millimeters/second. Many of the features listed above can be derived by evaluating the diameter of the pupil at a first image, the diameter of the pupil at a second image, and a length of time between the two images, as would be readily contemplated by a person skilled in the art. Furthermore, a person skilled in the art would readily understand that dilation latency, dilation velocity, dilation amplitude, and dilation percentage can be similarly calculated based on the data provided at 320.

Some examples of 330 provide for interpolating or extrapolating pupillary measures based on the trajectory observed of the collected image data.

Determining Health Status Based on Pupillary Features

Methodology 300 then provides for, at 340, determining a health status based on the pupil feature identified in 330. In some examples of 340, the features, as determined at 330, are compared to corresponding values of healthy individuals in order to identify abnormalities. In some examples, the features are compared to longitudinal data of the user; variations in currently-measured values from an established longitudinal baseline (individual) can be indicative of a disease state or a performance measure for disease. In some examples of 340, an individual user baseline is established over longitudinal use of a system 200 and a notification is provided when the pupil feature identified in 330 deviates from the established individual baseline by 1.5 standard deviations or by another, pre-determined threshold deviation. For example, the threshold deviation varies according to disease state. In some examples, 340 relies on a universal, or external, database of healthy individuals until the individual user has provided twenty separate PLR measures according to methodology 300. For instance, the user may provide 10, 11, 12, 13, 14, 15, 16, 17, 18, 19, 20, 21, 22, 23, 24, or 25 separate measures related to a specific condition or disorder. Then, the system can determine a significant deviation from that individual's baseline. If the individual has a specific disease (e.g., neurodegenerative disorder) the system could perform measures relative to that disorder and detect progression of the disease or disorder based on deviation form the user's business.

In some examples of methodology 300, the image data includes data of both eyes of a user. At 330, each pupil's reflex is analyzed separately; but, at 340, the features of the two are analyzed together to determine a health status, as varying pupillary light reflexes between each eye can be telling of a diseased state (e.g. stroke).

Providing Alerts Based on Disease/Neurophysiological Status

In some embodiments of methodology 300, an alert is provided based on the received data. For example, if a digital marker for a disease is detected, then a pre-disease detection alert is received by system 100, and presented, for example, on display 112. In some embodiments, an audio alert can supplement or replace a graphical alert. The user is thus made aware of developing diseases, disorders, or disease precursors and can take further action. Other information described above, such as a suggestion to contact a physician for a physical examination, may also be received and presented to the.

EXAMPLES

The following examples are provided to better illustrate the claimed invention and are not intended to be interpreted as limiting the scope of the invention. To the extent that specific materials or steps are mentioned, it is merely for purposes of illustration and is not intended to limit the invention. One skilled in the art may develop equivalent means or reactants without the exercise of inventive capacity and without departing from the scope of the invention.

Example: Display Delivering Visible Light Stimulus

In some examples, as disclosed herein, the display of a device (mobile device, mobile phone, tablet, virtual reality headset, etc.) may be utilized to deliver a visible light stimulus to trigger a PLR that can be measured. Accordingly, following are examples of how the disclosed systems and methods may integrate the use of a display to deliver a visible light stimulus.

For instance, the qualities and features of the visible light stimulus delivered by a display may be modified. Particularly, displays as disclosed herein (including LCD and LED displays) have a wide range of intensities and frequencies of visible light that are capable of emitting, and therefore allow for a wide range of different types and intensities of visible light stimulus that may be utilized to trigger a pupillary light reflex.

Accordingly, the display may include a variety of pixels and a control system associated with the device can deliver instructions to the display to emit light at a certain frequency and intensity. In some examples, various portions of the display or pixel groups of the display may be controlled to emit different frequencies and/or intensities of light. In other examples, all of the pixels of a display may be controlled to emit the same frequency and intensity of brightness.

In some examples, the display may emit white light from all of the pixels of the display at the highest brightness/intensity possible by the system 100 in order to deliver a visible light stimulus. In some examples, the pixels may be controlled to emit light that is limited to the spectrum of wavelengths in the green visible light spectrum (e.g. around 510 nm), red visible light spectrum (e.g. around 600 nm), or around blue visible light spectrum (e.g. around 450 nm) or spectral ranges in-between.

In some examples, the system may provide a stimulus at a first set of wavelengths and a second set of wavelengths and compare the results to output a health indication. For instance, the comparison may be utilized to screen for abnormal gaining of a user's eyes. In some examples, the text or instructions to the user may be displayed in a text color/background combination on the display that is the least stimulatory to the user's pupillary light reflex (e.g. red text on a black background).

Additionally, the system may use various methods to determine the features and qualities of the visible light stimulus emitted by a display. For instance, in some examples, an application that tests a user's PLR using a display to deliver the visible light stimulus may have a predetermined color/wavelength and intensity that is delivered each time. For instance, the system may provide instructions to the display to emit white or green light at the highest intensity possible by the system (e.g. based on the mobile device's power delivery thresholds and the output limits of the display).

In other examples, the system may first determine wavelengths and/or intensities of light to deliver as a visible light stimulus. For instance, FIG. 10 provides an exemplary method for determining an amount of visual stimulus to provide at a display.

In one example, methodology 1400 begins by receiving first image data when no light stimulus is provided, at 1410. For example, camera 114 of system 100 receives image data of a user without providing light stimulus from the display 112 or sensor 116. Accordingly, this allows the system to determine the ambient light level based on the contrast level of the image. In some examples, the system 100 may process data output form an ambient light sensor before the light stimulus is provided to determine the ambient light level.

Methodology 1400 then provides for determining the features of a visible light stimulus to provide (e.g. wavelength and amount of luminous flux) 1420, based on the first image data and/or ambient light sensor data received from 1410. In some examples, the amount of luminous flux and/or wavelength of visible light stimulus is additionally based on historical user health data, and/or based on a desired type of pupillary response. In some examples, the amount of luminous flux to deliver is determined based on the amount that would stimulate a maximum pupillary constriction of the user's pupil. In other examples, the amount of luminous flux may be the highest amount of luminous flux necessary to trigger a threshold PLR, and therefore minimize the discomfort to the user.

Accordingly, in some examples of 1420, other features of the visible light stimulus output from the display are determined. For example, a wavelength of light (or color of light within the visible light spectrum) to be emitted may be determined. For instance, each eye of a user has melanoptic receptors that are activated by different colors. Therefore, 1420 provides for controlling the wavelength (or color) of light to activate certain melanoptic receptors in the user's eye and certain receptor pathways. In some examples, these pathways allow delineation of diseases mediated by particular receptor pathways.

Methodology 1400 then provides for determining an area of the display to output the visible light stimulus 1430. In some examples, an entire display surface area is used and this determination is not made. In other examples, only a portion of the display surface area is used. In some examples, the only a portion of the display near the user's eyes is used as determined by processing image data form the camera and/or infrared image detection system. In some examples, by modifying the area of the display utilized to deliver the visible light stimulus, the total luminous flux may be increased or decreased proportionally.

In some examples of methodology 1400, the qualities of the visible light stimulus and the area of the display to output the visible light stimulus (e.g., 1420 and 1430) are determined simultaneously, or in any order.

Methodology 1400 then provides for outputting the determined amount of luminous flux on the display, at 1440.

In some examples of methodology 1400, additional image data of the eye is received after the luminous flux is output. In some examples, the luminous flux is adjusted based on the received image data.

Example: Infrared Measurements of Pupillary Light Reflex

Figure 12:
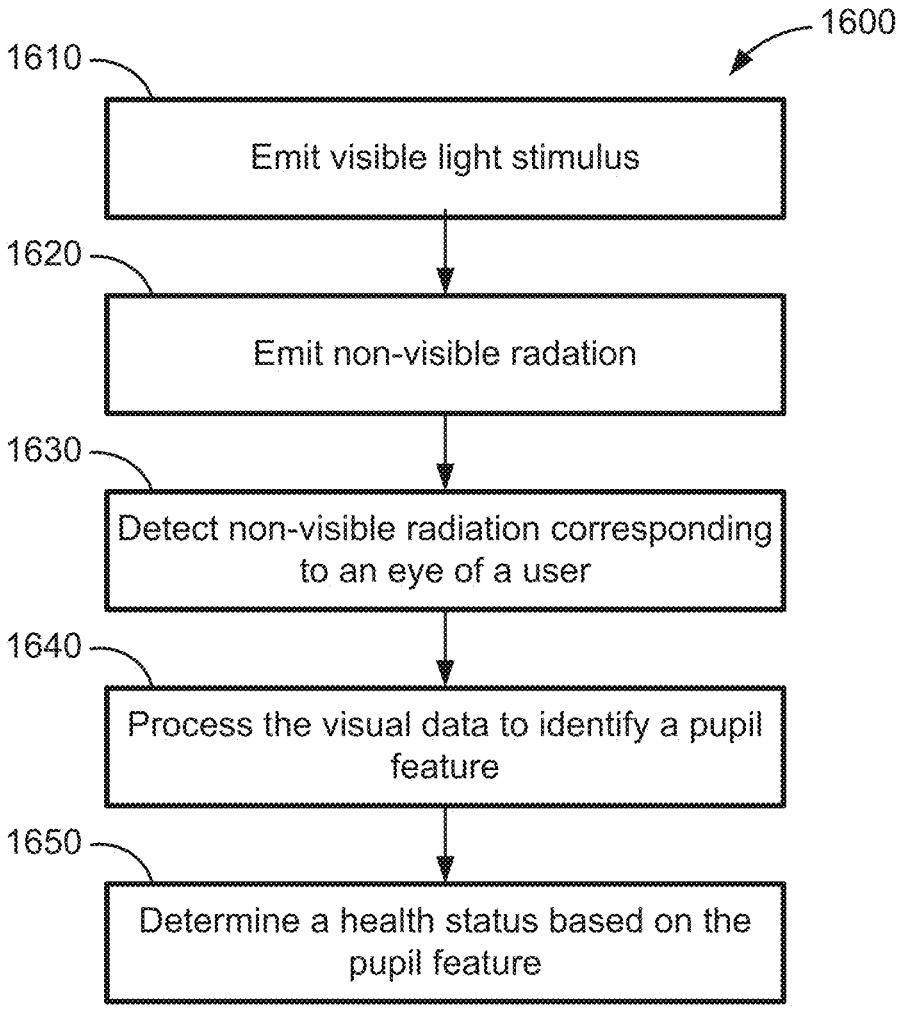
FIG. 12 shows an exemplary methodology for measuring pupillary response with non-visible light, according to an embodiment of the present disclosure.

In some examples, the disclosed technology captures images of the eye using a non-visible radiation/emission, for instance an infrared camera, for processing to evaluate PLR. Accordingly, in some embodiments, this methodology may be used in low ambient lux environments where utilizing visible light for image capture to evaluate the pupillary response would trigger additional, confounding pupillary responses. For example, the sensor 116, infrared emitter, and/or the display 112 of FIG. 1 can provide a non-visible light emission. In some examples, the camera 114 is an infrared camera and includes one or more infrared light emitters. In some examples, the camera 114 is an infrared camera that detects ambient infrared light. FIG. 12 shows an exemplary methodology 1600, which can be performed on systems 100 and/or 200 of FIGS. 1 and 2, respectively.

Methodology 1600 provides for, at 1610, emitting a visible light stimulus by a display or flash (e.g., the display 112 or the sensor 116 of FIG. 1). For example, the visible light stimulus has a wavelength greater than 1000 nm. The visible light stimulus is directed towards the face of a user. This visible stimulus is configured to initiate a pupil response in an eye of the user.

Methodology 1600 then provides for, at 1620, emitting a non-visible light by a display (e.g., the display 112 or the sensor 116 of FIG. 1, e.g. an infrared emitter). The non-visible light is configured to illuminate the user's face sufficient to cause a high enough image contrast (sufficiently high enough for pupil-iris segmentation). Therefore, the infrared measurement implementation makes use of the high-image contrast that is provided by infrared light generally. For example, an infrared system may emit non-visible light for measurement with a wavelength between 600 nm and 1000 nm. In other examples ambient infrared light will be sufficient to illuminate the user's face and may be detected by the infrared system.

Because 1620 provides the illumination sufficient to provide high enough image contrast, methodology 1600 requires less visible stimulus at step 1610 than methodologies which rely only on visible stimulus (including, for example, methodology 300 of FIG. 3). Therefore, methodology 1600 is able to more accurately trigger pupil responses, because the system does not need to use visible light to illuminate the user's face in order to capture images of the eye after delivering the visible light stimulus.

Methodology 1600 further provides for receiving, at 1630, image data corresponding to an eye of a user. In some examples, the image data received is a set of images or a video. In some examples, the set of images are collected at regular intervals (e.g., intervals measured in seconds, milliseconds, and/or microseconds) for a period of time (e.g., over one minute, two minutes, three minutes). In some examples, the image data received at 1630 is received from an infrared camera.

Methodology 1600 further provides, at 1640, for processing the image data to identify a pupil feature. For example, the received image data is processed according to any of the methodologies discussed with respect to 330 of methodology 300 of FIG. 3. Methodology 1600 then provides for, at 1650, determining a health status based on the identified pupil feature. For example, the health status is determined according to any of the methodologies discussed with respect to 340 of methodology 300 of FIG. 3.

Therefore, methodology 1600 avoids confounding pupillary response results with additional, unintentional stimulus.

Example: Ambient Light Sensing

Some examples of the present disclosure provide for sensing ambient light conditions to be utilized as inputs for the disclosed system and methods in order to execute certain features or measurement methods. For instance, the ambient light levels may be sensed to determine whether they are: (1) sufficient to provide image data of adequate quality to determine the various pupil features discussed herein using a camera, (2) below a threshold lux that requires an infrared sensing system to capture images of the pupils with sufficient quality to process them and identify various pupillary features disclosed herein, or (3) below a threshold making it sufficiently dark to utilize a display to provide a visible light stimulus, so that the contrast between the lux of the visible light stimulus emitted by the display and the ambient light lux is sufficient to trigger a PLR.

Figure 13:
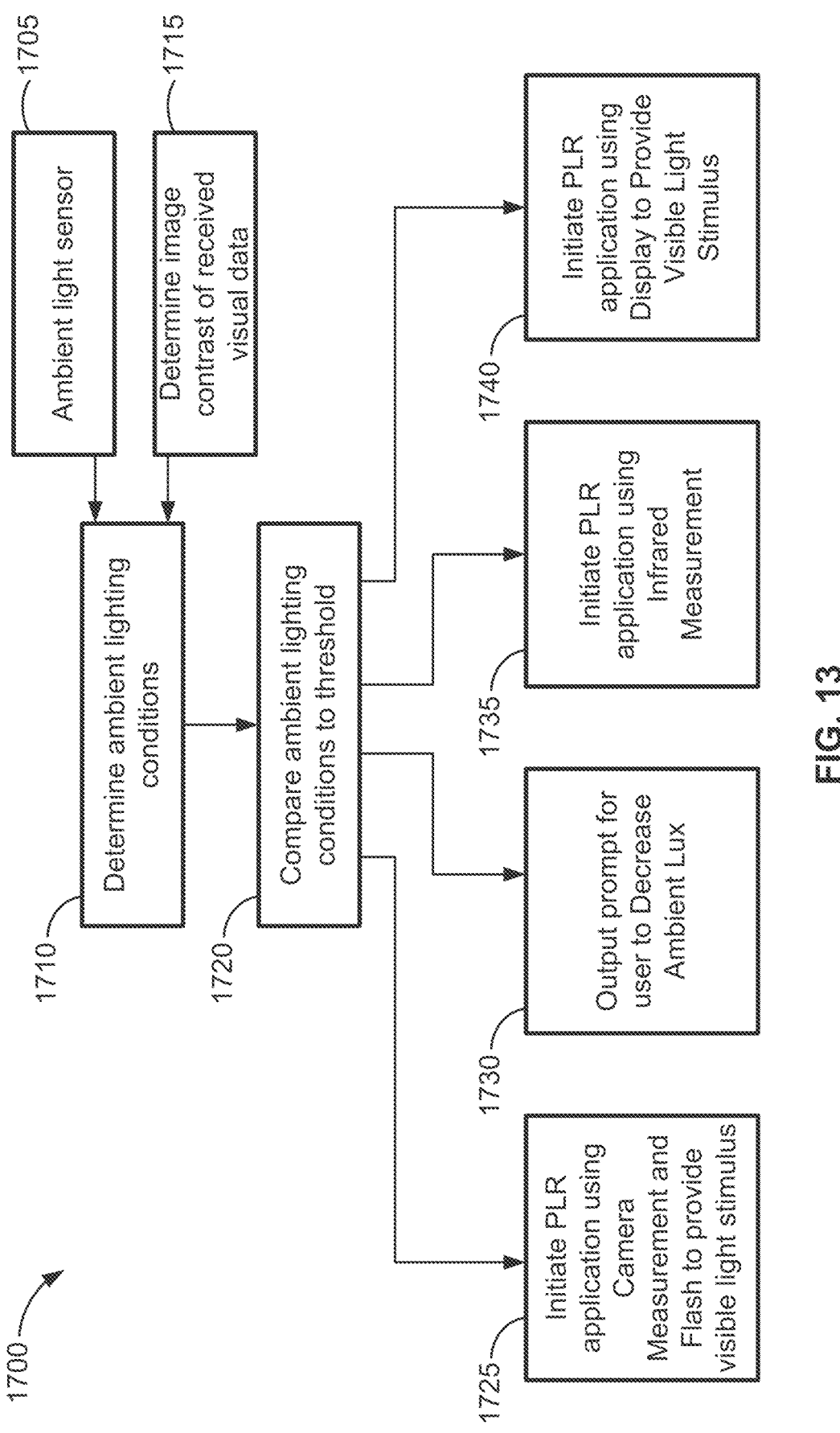
FIG. 13 shows an exemplary methodology for determining proper image contrast, according to an embodiment of the present disclosure.

FIG. 13 shows an exemplary methodology 1700 for evaluating ambient light conditions, according to an embodiment of the present disclosure. Methodology 1700 can be performed by systems 100 and/or 200 of FIGS. 1 and 2, respectively.

Methodology 1700 provides for, at 1710, determining ambient light conditions 1710. This may be performed by using an ambient light sensor 1705 as disclosed herein and/or by determining an image contrast on a set of received visual data 1715 by a camera and/or infrared image system. For example, the image contrast may be determined with respect to brightness, color, saturation, and/or any other suitable image analysis techniques.

Methodology 1700 then provides for, at 1720, comparing the ambient lighting conditions to a threshold 1720. Accordingly, the system may then execute various an action based on the comparison. For instance, if the ambient lux and/or image contrast is above a certain threshold (e.g. above 50, 60, 65, 70, 75, 85, 90, 95, or 100 ambient lux), the system may initiate a PLR application using a camera based measurement 1725. For instance, the threshold may be based on whether pupil-iris segmentation can be performed based on the image data provided. In some examples, the threshold utilized in 1725 is based on whether pupil-iris segmentation can be performed with a certain accuracy threshold and/or confidence measure.

Additionally, if the ambient lux and/or image contrast is above a certain threshold and the system is set to use a display as a visible light stimulus, the system may output a prompt to the user to decrease the ambient lux 1730. For instance, the user may turn off lighting in the room, close shades or move to a location in the room that is darker. In some examples, the system may continually monitor the ambient lux and provide an automatic notification when the ambient lux is sufficiently low to perform an assessment using a display to provide a visible light stimulus.

In another example, if the ambient lux and/or image contrast is below a certain threshold, and the system may initiate a PLR application using infrared measurement 1735. For instance, if the ambient lux is below a certain threshold, the image quality captured by a visible light camera may be too low to be accurate to assess PLR metrics. Accordingly, the system may automatically use an infrared based measurement system to capture images of the eye after delivering a visible light stimulus (that may be delivered using a display or a flash).

In another example, if the ambient lux is below a certain threshold, the system may initiate a PLR application using a display to provide the visible light stimulus 1740. For instance, a threshold based on experimental data may be utilized to determine the highest ambient lux that will still allow for a PLR response to be triggered using a display as a stimulus for a given display and power system of a given device. For instance, based on the maximum flux delivered by the display, a maximum ambient lux may be determined that will still allow for a large enough contrast between the flux delivered by the display and the ambient lux so that a user's PLR is triggered. In some examples, an ambient wavelength and intensity may be determined as certain types of ambient lighting including wavelengths (e.g. sunlight versus red indoor light) might record a higher intensity or flux visible light stimulus to trigger a user's PLR.

Example: Identifying Multiple Pupillary Responses from Ambient Light Changes

In some examples of the present disclosure, a method is provided to identify multiple pupillary responses triggered from changes in ambient lighting that are unwanted or in addition to the visible light stimulus. For instance, various environmental or additional lighting may trigger additional PLR responses that may introduce noise into the assessment of the PLR by triggering unintentional/additional pupillary light reflexes. These may include: (1) ambient lux and/or spectral composition of the ambient lighting may change during an assessment, or (2) visual prompts/instructions, emitted by the display after delivering of the visible light stimulus; or (3) other sources.

FIG. 11 shows an exemplary methodology 1500 for identifying and tagging unintentional pupil responses, according to an embodiment of the present disclosure. First, at 1510, the system may tag a first pupil response based on the received image data. For example, the first pupil response includes a change in any of the pupil features as discussed herein.

Methodology 1500 then provides for, at 1520, receiving second image data, after the originally-received image data.

Methodology 1500 then provides for, at 1530, determining a change in lighting conditions. For example, the change in light conditions can be determined based on a brightness difference between the received image data from 1510 and the received second image data from 1520. In other examples, an ambient light sensor may be utilized to detect changes in ambient lux before and after delivery of the visible light stimulus.

Methodology 1500 then provides for tagging a second pupil response in the second image data, at 1540. For example, if the second image data is a series of images, 1540 provides for identifying the image or images which occur simultaneously, or close in time afterwards to the change in lighting conditions. In some examples, the second pupil response is identified as any one of the pupil features discussed herein.

Example: Pre-processing & Processing the Data

In some examples of 330, the received image data is pre-processed. Exemplary pre-processing techniques are discussed herein.

Frames in the sequence are smoothed to de-noise the system of natural fluctuations in the pupil, color variance in the irises, as well as variance caused by the device itself. A Gaussian smoothing operator can be used to slightly blur the images and reduce noise. The 2D Gaussian equation has the form:

$$G(x, y) = \frac{1}{2\pi\sigma^2} e^{\frac{-(x^2+y^2)}{2\sigma^2}} \qquad \text{Equation 1}$$

where sigma is the standard deviation of the distribution, which may be given by:

$$\sigma = \sqrt{\frac{1}{N} \sum_{i=1}^{N} (x_i - \mu)^2} \qquad \text{Equation 2}$$

where x is the $i^{th}$ PLR measurement, $\mu$ is the mean PLR, and N is the total number of PLR measurements. In some embodiments, a particular measurement of PLR that is probabilistically significant, such as +/-one standard of deviation or +/-1.5 standards of deviation, trigger an alert that an anomaly was detected in the neurological system. In some such embodiments, the alert may be for a particular pre-disease condition. In other embodiments, the alert may simply indicate that an anomaly was detected.

In some examples of the present disclosure, PLRs are represented as smooth Fourier transformations. For example, when using a histogram representation of the smoothed grayscale frames, a threshold function binarizes the images. This threshold function can be determined by the distinction between dark and light pixels on the histogram. Based on this, the images can be binarized in such a way that distinguishes the sclera from the pupil by labelling white parts of the image with a 1, and black parts of the image with a 0. This effectively generates a black square with a white circle representing the pupil clearly for analysis. Pupils are generally shaped as ellipses, but can be represented as a circle by averaging the axes. Diameter can be measured in pixels between the two white pixels farthest away from each other. This pixel measurement can be converted to millimeters using a fiducial of known dimensions held near the eye.

For example, depth of the smartphone from the face might be determined using a dot projector in a smartphone.

The differential equation that describes a pupillary light reflex in terms of pupil diameter flux as a function of light can be written as follows:

$$\frac{dM}{dD}\frac{dD}{dt}(t) + 2.3026\tanh^{-1}\left(\frac{D-4.9}{3}\right) = \qquad \text{Equation 3}$$

$$5.2 - 0.45\ln\left(\frac{\Psi[t-\tau\tau]}{4.8118*10^{-10}}\right)$$

$$M(D) = \tanh^{-1}\left(\frac{D-4.9}{3}\right) \qquad \text{Equation 4}$$

D is measured as the diameter of the pupil (mm), and $\Phi(t-\tau)r$ represents the light intensity that reaches the retina in time t. Thus, the using the data from the video (e.g. the diameter of the white circle representing the pupil in each frame, the time between frames and the conversion between pixels to millimeters), the differential equation above may be utilized to determine the pupil velocity. The pupil velocity both in reacting to the flash of light (decreasing in diameter) and recovery (increasing in diameter) can be determined.

In some examples, pre-processing includes cropping the footage to include a region of each individual eye. This could be implemented by applying the simple heuristics of the known structure of the human face. The footage can then be submitted for processing, which includes, for example, deconstructing the received visual stimulus into a series of images to be processed one by one. Images are manipulated to eliminate the aberrations of eye glasses, blinking and small hand movements during image capture. Pupil boundary detection using entropy of contour gradients may be used to extract the size of each pupil and create data series which could be visualized.

In some embodiments, an eye tracker may be used to capture frames of eyes with different levels of dilation. The user can manually tag the pupil diameters for each frame. Using the tagged data, a segmentation model can be trained using the tagged pupils. For example, U-Net or an analogous service might be used to output shapes from which diameter may be inferred. A pipeline may be implemented to process recorded frames of video and graph the pupil dilation over time.

In some examples of processing the data, hue, saturation, and brightness values are used to filter the received image data. For example, pixels may be filtered out if the pixels have a "V" value (which represents brightness) of greater than 60. In another example, the pixels may be filtered based on LAB values, where "L" represents a brightness of the pixel, and "A" and "B" represent color-opponent values. Because the pupil is the darkest feature of the eye, pixels may be filtered out which have an "L" value greater than 50, thereby leaving only the pixels which are relatively darker and more likely to include the pupil.

Additional exemplary processing steps include (1) duplicating the filtered image, discarding what has been filtered out to just show the region of interest (ROI), (2) converting the filtered ROI pixels to grey scale, (3) filtering grey scale pixels based on brightness or intensity values, for example, by filtering pixels having an L value higher than 45, (4) scanning the remaining pixels for contours and convex shapes, (5) scanning the pixels for incremental gradients in grey scale values of pixels, (6) constructing shapes based on, or defined by, the contours, (7) filtering those shapes based on size and circularity, (8) determining a surface area of pupil region and iris region, and (9) determining a relative change in the two regions over time.

In some examples of filtering based on circularity, the device filters out values which are not at or around a 1.0 circularity value. For example, circles have circularity values at or near 1.0, while an elongated ellipse may have a circularity value of around 0.25.

Example: Pupil Segmentation

The present disclosure provides for pupil segmentation methods. The image data of the eyes can be segmented into three main parts: pupil, iris, and sclera. Image segmentation algorithms might be used to provide the desired segmentation.

Figure 6:
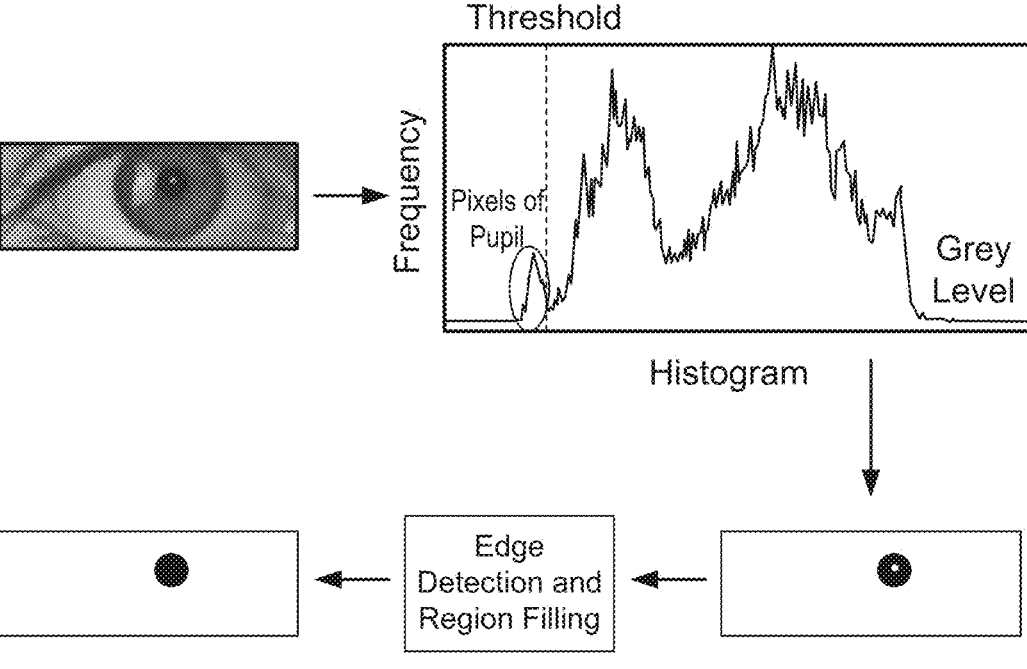
FIG. 6 shows an exemplary pupil segmentation methodology, according to an embodiment of the present disclosure.

FIG. 6 shows an exemplary pupil segmentation process. First, a greyscale image of an eye is received. Then, a balanced histogram is created based on a grey level of each of the pixels. For example, balanced histogram thresholding segmentation, K-means clustering, or edge detection and region filling might be used. An exemplary balanced histogram segmentation algorithm sets a threshold grey level for the pixels to determine which correspond to the pupil. The pixels corresponding to the pupil will be the darkest pixels.

In one example, K-means clustering chooses k (e.g., k is 4 in this example) data values as the initial cluster centers. The distance between each cluster center and each data value is determined. Each data value is assigned to the nearest cluster. The averages of every cluster are then updated and the process repeated until no more clustering is possible. Each cluster is analyzed to determine which cluster includes the pixels of pupil, getting the segmentation result. This method can be used to segment the interest area from the background based on the four main parts in the eyes having different colors: black pupil, white sclera, colored iris and skin background.

The method shown in FIG. 6 further provides for edge detection and region filling, which enhances the image and links the dominant pixels of the pupil. Holes of certain shapes and sizes are filled to get the final results of segmentation.

After segmentation, the area of the pupil is determined, measured in pixels. This pixel measure is converted to a physical size (e.g. millimeters) based on a scale of the camera which collected the image data.

Example: Measuring Pupil Diameter

Figure 7:
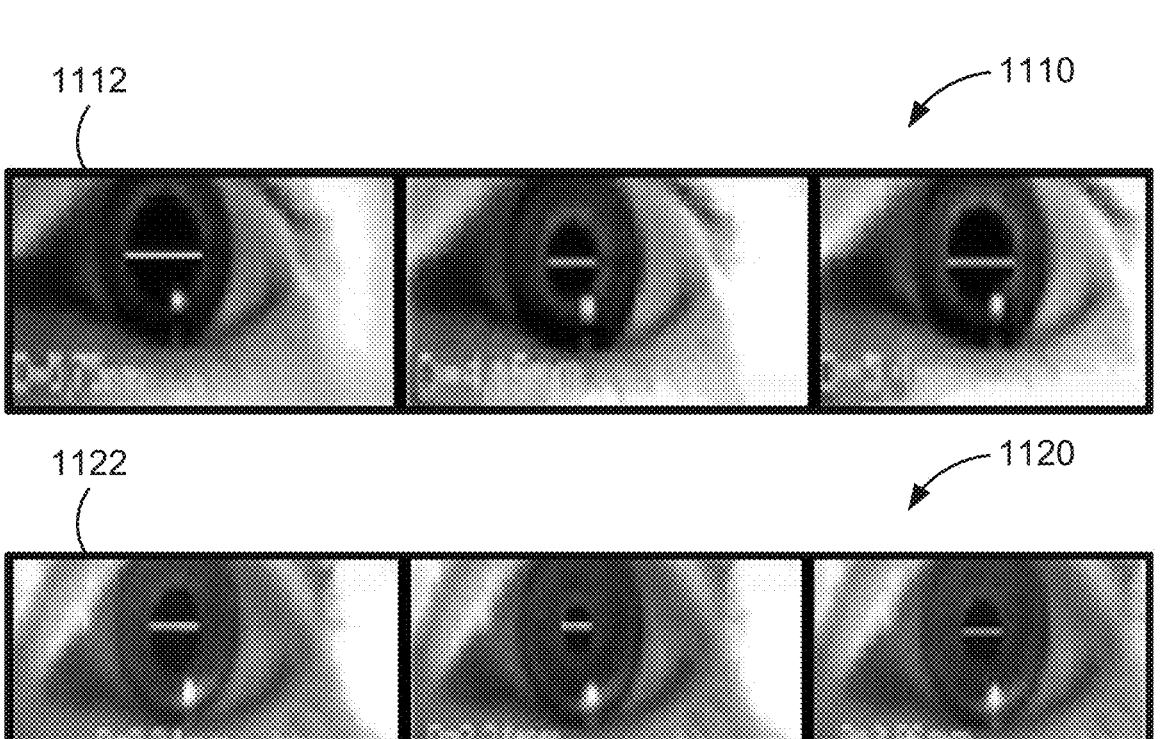
FIG. 7 shows exemplary pupillary constriction, according to an embodiment of the present disclosure.

FIG. 7 shows exemplary pupil diameter measurements. For example, 1112 and 1122 show a baseline pupil diameter for subjects 1110 and 1120, respectively. Subject 1110 is healthy and subject 1120 has Alzheimer's Disease. MCV and MCA can be calculated based on the methods discussed herein.

Example: Pupillary Features Output

Figure 4A:
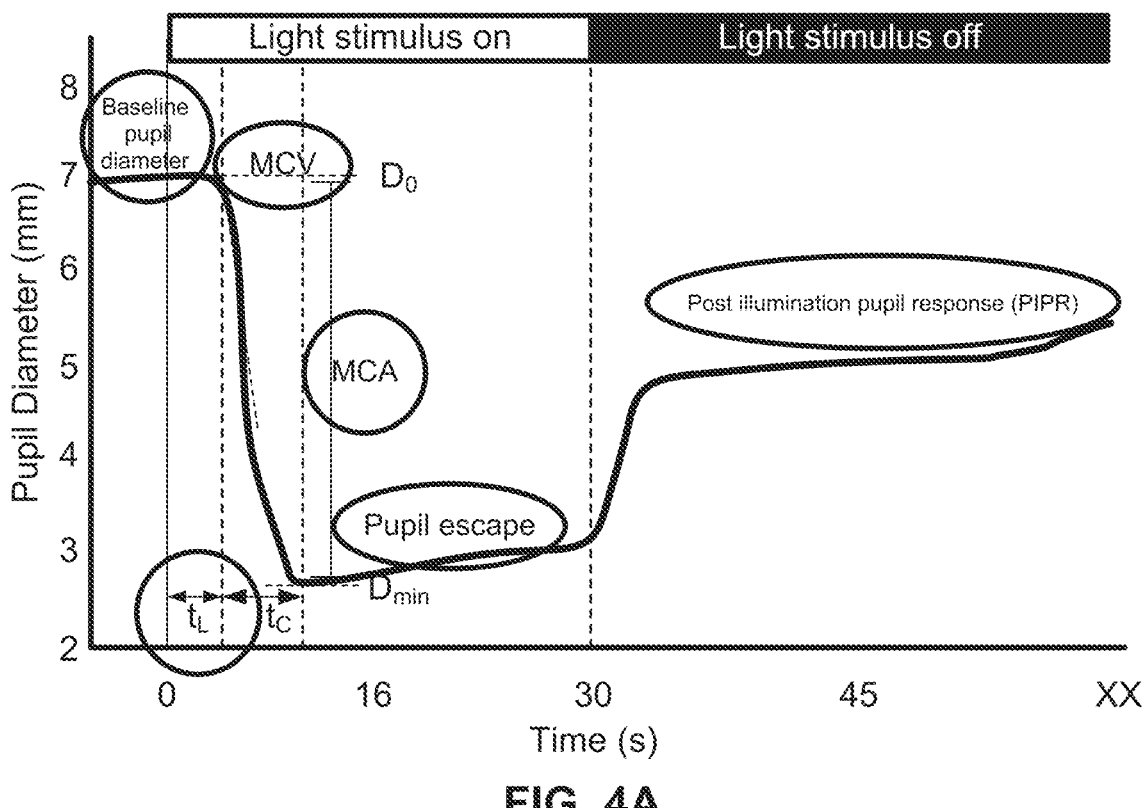
FIG. 4A shows an exemplary pupillary response separated into sub-phases, according to an embodiment of the present disclosure.

FIG. 4A shows an exemplary pupil response curve and the various features that can be identified at different points in the curve. For example, these features are analyzed with respect to methodology 300, discussed above. FIG. 4A demonstrates that when a light stimulus is on, a baseline pupil diameter is first detected; MCV, MCA, and pupil escape are subsequently evaluated. When the light stimulus is turned off, a post-illumination pupil response (PIPR) can be evaluated.

Figure 4B:
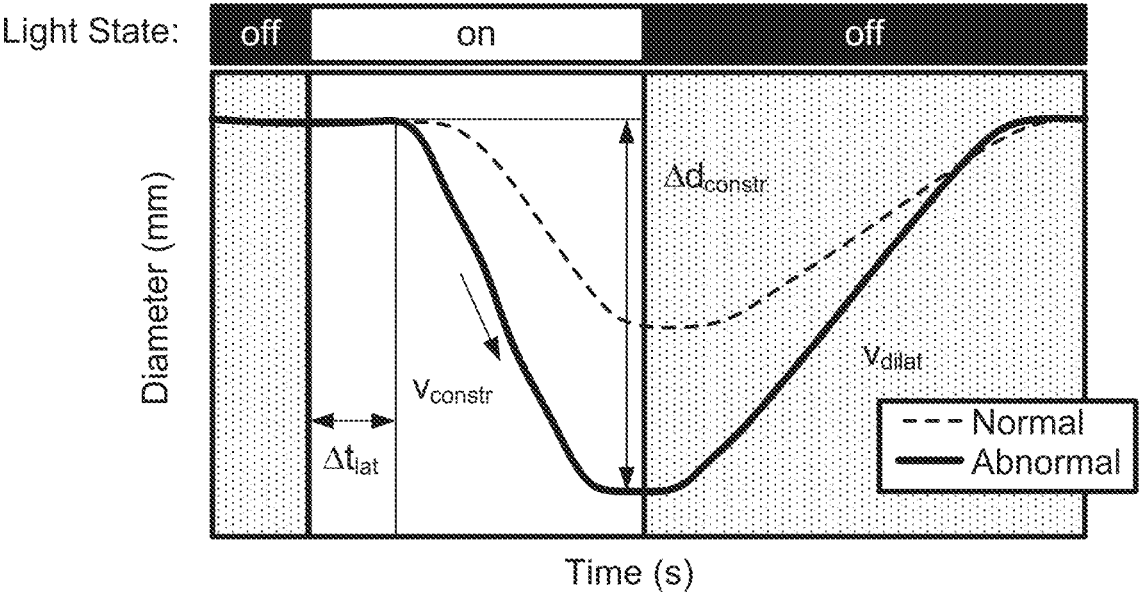
FIG. 4B shows exemplary pupillary responses as compared between a healthy and unhealthy subject, according to an embodiment of the present disclosure.

FIG. 4B shows another exemplary PLR curve, including: (1) latency, (2) constriction velocity, (3) constriction amplitude, (4) constriction percentage, and (5) dilation velocity. The dashed line shows an abnormal PLR curve with increased latency, slower velocities, and diminished amplitude than the normal PLR curve shown by the solid line.

Example: Predicting Health Status based on Pupil Features

Figure 5:
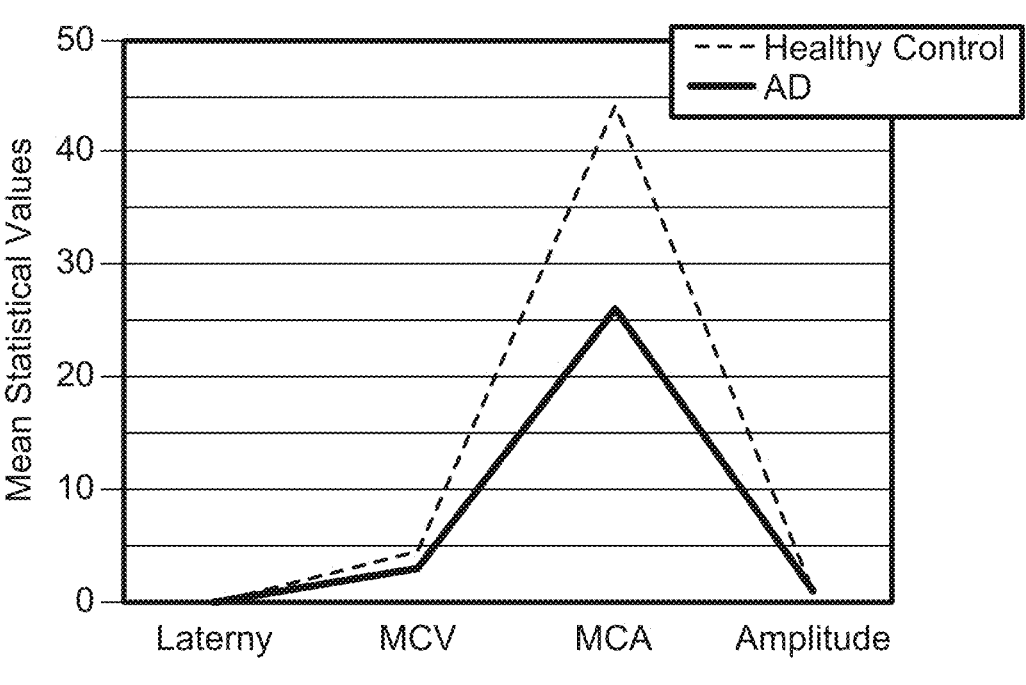
FIG. 5 shows average measured pupillary responses, according to an embodiment of the present disclosure.

Various aspects of 340 of methodology 300 of FIG. 3 can be used to identify whether the user has various disease states, disease severity, or other health ailments. FIGS. 5-7 below demonstrate exemplary data that corresponds to exemplary health statuses.

FIG. 5 shows average measured pupillary responses correlate to Alzheimer's Disease. For example, FIG. 5 shows that latency, MCV, MCA and Amplitude have significant differences between a group with cognitively healthy patients and a group with Alzheimer's Disease patients.

In some examples, a health status is determined based on a difference in a PLR measure in response to different wavelengths of visual light stimulus. For instance, age related changes in pupillary response may be observed by comparing the PLR of a user using light with green spectrum as the visible light stimulus with the PLR of a user using white light as the visible light stimulus.

Example: Software Application

In some examples of system 200 of FIG. 2 and methodology 300 of FIG. 3, a smartphone is held in hand in and in a natural controlled viewing spatial distance from a user's face (e.g. within 6-24 inches horizontally from the user's face, within 6 inches vertically from the eye level and within 6 inches horizontally (right to left on the user) of the user's nose, though other distances may be possible), indoors with controlled ambient light. In some embodiments, holding the smartphone in this position for a controlled amount of time (e.g. at least 5 seconds), will activate an App (via sensors and software) to video record a subject's face (particularly the eye and reflex of the pupil) at 60+ or 120+ frames per second in HD upon being catalyzed by a stimuli of a brief intense flash of light provided from the display, touchscreen, flash or other light source on the smartphone during recording. This flash of light is focalized and of known intensity from both its origin and can the intensity of light reaching the pupil can also be determined by the square of the distance from the source and the pupil. Thus, images of the user's face are captured before, during and after the brief flash of light. In some embodiments, the recording starts at least 1 second and not more than 5 seconds before the flash of light and continues for at least 3 seconds and not more than 8 seconds after the flash of light. Of note, the intensity that reaches the pupil can be inferred by the square of the distance between pupil and light source.

Example: Alignment of Facial Features

The present disclosure contemplates an exemplary health application, which renders a template having alignment marks for the user's key facial parts on the display for client device. The health application instructs the user to align key facial parts with alignment marks represented on a smart phone screen. The user's facial parts are selected for alignment to ensure trigonometric consistency in depth and angle given these facial parts remain fixed over time in three dimensional space and cannot be voluntarily or involuntarily changed by the user. The device may provide an indicator, such as a green light, when the measurement is about to be taken. Health application flashes a light on client device and captures a video of the user's eye with a high definition camera that is one of sensors.

To measure PLR, the user is given instructions for aligning their eyes in the camera. This provides the proper image size for further image processing and pupil measurement. The camera session is started to detect the user's face and obtain images of the user's eyes. The background color and phone brightness (if using front-facing camera) are adjusted (or torchLevel adjusted) to create various levels of lightness/darkness. The images may be processed in real-time including segmentation, obtaining the diameter of the pupil and tracking the time for measuring pupil contraction speeds. Finally, results of the measurements including reaction time for both eyes, contraction speeds, and the percentage of pupil closure may be presented to the user.

Example: Automatic Facial Detection

Automatic facial detection is possible using the tip of the nose and two pupils. In some embodiments, the controlled spatial distance mentioned above is achieved by the user aligning their face with the 3 red triangular dots on the viewfinder (2 for the pupils, 1 for the tip of the nose). Via machine vision, the pupils are recognized as aligned with the red dots and the nose tip (based on RGB color of the nose skin) is aligned with nose tip. Then ambient light sensor is used to check for any ambient light (noise) that would add confounding variables to the measure. If alignment (depth/angle) and lighting are sufficient, then the red dots turn green and the user is notified that the measure is ready to be taken in a certain amount of time. FIG. 8 indicates this process.

A visible light stimulus is then provided and video is captured. Facial detection may be accomplished using one or more frames of the video. Thus, after capture of the video above, with machine vision based algorithmic assistance, the smartphone automatically detects the pixel-based locations of the tip of the nose, as well as the two pupils (which may also be projected on the screen), to ensure measurements are trigonometrically and spatially consistent. The special geometry and distance of these three reference points are cannot be voluntarily nor involuntarily changed over time by the facial muscles, further ensuring control and consistency.

Consequently, faces and eyes can be detected (as shown in FIGS. 12-13). The input video/video frames are in grayscale in some embodiments. If a face is detected in the video, the system will proceed to detect eyes within the coordinates of the face. If no face is detected, the user will be notified that the given video does not meet the criteria for effective detection.

A face recognition algorithm to guide the user during a Pre-Capturing phase in real time may be used. In some embodiments, this could be achieved by using the OpenCV (Open Source Computer Vision Library), ARKit (Augmented Reality Kit), or other facial recognition mechanisms. Using face recognition, the eye position on the image can be identified and the user directed to manipulate the device to situate the camera in the desired position. Once the camera is situated—the image data capturing phase may occur. Modern smartphones may have the capacity to emit over 300 nits (1 candela/m2). Video footage can be as short as 10-20 seconds may be sufficient to capture enough data for PLR analysis. Modern smartphone camera(s) (e.g. scamera 114 of FIG. 1) are used to capture the video before, during and after a visible light stimulus.

In some embodiments, face capture in combination with face and eye recognition might also be used in performing a PLR measurement. Some facial recognition frameworks, such as Vision Framework, can detect and track human faces in real-time by creating requests and interpreting the results of those requests. Such tool may be used to find and identify facial features (such as the eyes and mouth) in an image. A face landmarks request first locates all faces in the input image, then analyzes each to detect facial features. In other embodiments, face tracking, for example via an augmented reality session, might be used. An example of one such mechanism is ARKit. Using such a mechanism the user's face may be detected with a front-facing camera system. The camera image may be rendered together with virtual content in a view by configuring and running an augmented reality session. Such a mechanism may provide a coarse 3D mesh geometry matching the size, shape, topology, and current facial expression and features of the user's face. One such mechanism may be used to capture and analyze images or multiple mechanisms might be combined. For example, one might be used to capture images, while another is used to analyze the images.

Selected Embodiments I

Although the above description and the attached claims disclose a number of embodiments of the present invention, other alternative aspects of the invention are disclosed in the following further embodiments.

1. A system for evaluating pupillary light reflex, comprising:
    a mobile device comprising a front and a back;
    a camera located on the front of the mobile device;
    a display located on the front of the mobile device;
    a processor; and
    a memory having stored therein a plurality of code sections executable by the processor, the plurality of code sections comprising instructions for:
        emitting at least one visible light stimulus by the display;
        receiving, from the camera, image data corresponding to at least one eye of a user;
        processing the image data to identify at least one pupil feature; and
        determining a health status based on the at least one pupil feature.

2. The system of embodiment 1, wherein the instructions further provide for outputting the health status at the display.

3. The system of embodiment 1, wherein the camera is an infrared camera.

4. The system of embodiment 1, wherein the at least one pupil feature includes at least one of: pupil response latency, constriction latency, maximum constriction velocity, average constriction velocity, minimum pupil diameter, dilation velocity, 75% recovery time, average pupil diameter, maximum pupil diameter, constriction amplitude, constriction percentage, pupil escape, baseline pupil amplitude, post-illumination pupil response, and any combination thereof.

5. The system of embodiment 1, wherein determining a health status based on the at least one pupil feature further comprises:
    determining a difference between each of the at least one pupil feature and a corresponding healthy pupil measurement, wherein the corresponding healthy pupil measurement is retrieved, by the processor, from an external measurement database; and
    determining the health status based on the determined difference for each of the at least one pupil feature and the corresponding healthy pupil measurement.

6. The system of embodiment 1, wherein emitting at least one visible light stimulus by the display further comprises emitting visible light only in the red, blue, or green spectrum.

7. The system of embodiment 1, wherein emitting at least one visible light stimulus by the display further comprises:
    receiving first image data of the at least one eye when no light stimulus is provided by the display;
    determining an amount of luminous flux to provide based on the first image data;
    determining an area of the display to output the determined amount of luminous flux; and
    outputting the determined amount of luminous flux on the determined area of the display.

8. The system of embodiment 7, further comprising receiving second image data of the at least one eye after outputting the luminous flux.

9. The system of embodiment 8, further comprising adjusting the output luminous flux based on the second image data.

10. The system of embodiment 1, further comprising:
    tagging a first pupil response based on the received image data;
    receiving second image data;
    determining a change in lighting conditions based on the second image data; and
    tagging the second pupil response.

11. A method of evaluating pupillary light reflex, comprising:
    emitting at least one visible light stimulus by a display located on a front of a mobile device;
    receiving, from a camera located on the front of the mobile device, image data corresponding to at least one eye of a user;
    processing the image data to identify at least one pupil feature; and determining a health status based on the at least one pupil feature.

12. The system of embodiment 11, further comprising outputting the health status at the display.

13. The method of embodiment 11, wherein processing the image data to identify at least one pupil feature further comprises preprocessing the received image data.

14. The method of embodiment 11, wherein determining a health status based on the at least one pupil feature further comprises:
    determining a difference between each of the at least one pupil feature and a corresponding healthy pupil measurement, wherein the corresponding healthy pupil measurement is retrieved, by the processor, from an external measurement database; and
    determining the health status based on the determined difference for each of the at least one pupil feature and the corresponding healthy pupil measurement.

15. The method of embodiment 11, wherein emitting at least one visible light stimulus by the display further comprises:
    receiving first image data of the at least one eye when no light stimulus is provided by the display;
    determining an amount of luminous flux to provide based on the first image data;
    and outputting the determined amount of luminous flux on the display.

16. A non-transitory machine-readable medium comprising machine-executable code, which, when executed by at least one machine, causes the machine to:
    emit at least one visible light stimulus by a display located on a front of a mobile device;
    receive, from a camera located on the front of the mobile device, image data corresponding to at least one eye of a user;
    process the image data to identify at least one pupil feature; and determine a health status based on the at least one pupil feature.

17. The non-transitory machine-readable medium of embodiment 16, further comprising: output the health status at the display.

18. The non-transitory machine-readable medium of embodiment 16, wherein processing the image data to identify at least one pupil feature further comprises preprocessing the received image data.

19. The non-transitory machine-readable medium of embodiment 16, wherein determining a health status based on the at least one pupil feature further comprises:

determining a difference between each of the at least one pupil feature and a corresponding healthy pupil measurement, wherein the corresponding healthy pupil measurement is retrieved, by the processor, from an external measurement database; and determining the health status based on the determined difference for each of the at least one pupil feature and the corresponding healthy pupil measurement.

20. The non-transitory machine-readable medium of embodiment 16, wherein emitting at least one visible light stimulus by the display further comprises:

receiving first image data of the at least one eye when no light stimulus is provided by the display;

determining an amount of luminous flux to provide based on the first image data; determining an area of the display to output the determined amount of luminous flux; and outputting the determined amount of luminous flux on the determined area of the display.

21. A method for evaluating pupillary light reflex, comprising:

receiving from an ambient light sensor, a set of lux data;

comparing the set of lux data to a threshold;

initiating a display based PLR application if the set of lux data is below the threshold, the display based PLR application comprising instructions to execute the following steps:

emitting at least one visible light stimulus by the display;

emitting non-visible light a predetermined time after emitting the at least one visible light stimulus;

receiving, from a camera, image data corresponding to at least one eye of a user;

processing the image data to identify at least one pupil feature; and determining a health status based on the at least one pupil feature.

22. The method of embodiment 21, further comprising providing a notification to a user to reduce the ambient lux if the set of lux data is above a threshold.

23. The method of embodiment 21, wherein the health status is abnormal aging of an eye of the user and the at least one visible light stimulus comprises light only in a green spectrum.

Selected Embodiments II

Although the above description and the attached embodiments disclose a number of embodiments of the present invention, other alternative aspects of the invention are disclosed in the following further embodiments.

1. A system for evaluating pupillary light reflex, comprising:

a hardware device comprising a front and a back;

an infrared camera located on the front of the hardware device;

a display located on the front of the hardware device;

an infrared emitter located on the front of the hardware device a processor; and a memory having stored therein a plurality of code sections executable by the processor, the plurality of code sections comprising instructions for:

emitting at least one visible light stimulus by the display;

emitting non-visible light by the infrared emitter;

receiving, from the infrared camera, image data corresponding to at least one eye of a user;

processing the image data to identify at least one pupil feature; and determining a health status based on the at least one pupil feature.

2. The system of embodiment 1, wherein the non-visible light comprises a light emission with a wavelength between 700 nm and 1000 nm.

3. The system of embodiment 1, wherein the at least one pupil feature includes at least one of: pupil response latency, constriction latency, maximum constriction velocity, average constriction velocity, minimum pupil diameter, dilation velocity, 75% recovery time, average pupil diameter, maximum pupil diameter, constriction amplitude, constriction percentage, pupil escape, baseline pupil amplitude, post-illumination pupil response, and any combination thereof.

4. The system of embodiment 1, wherein the hardware device comprises a virtual reality headset or a mobile device.

5. The system of embodiment 1, wherein the display is a touchscreen.

6. A method for evaluating pupillary light reflex, comprising:

receiving from an ambient light sensor, a set of lux data;

comparing the set of lux data to a threshold;

initiating an infrared measurement based application of the set of lux data is below a threshold comprising:

emitting at least one visible light stimulus;

emitting non-visible light a predetermined time after emitting the at least one visible light stimulus;

receiving, from an infrared camera, image data corresponding to at least one eye of a user;

processing the image data to identify at least one pupil feature; and determining a health status based on the at least one pupil feature.

7. The method of embodiment 6, further comprising:

providing a notification to a user to reduce the ambient lux if the set of lux data is above a threshold. The method of embodiment 6, wherein the at least one pupil feature includes at least one of: pupil response latency, constriction latency, maximum constriction velocity, average constriction velocity, minimum pupil diameter, dilation velocity, 75% recovery time, average diameter, constriction amplitude, constriction percentage, pupil escape, baseline pupil amplitude, post-illumination pupil response, and any combination thereof.

8. The method of embodiment 7, wherein the non-visible light comprises light with a wavelength between 700 nm and 1000 nm.

9. A non-transitory machine-readable medium comprising machine-executable code, which, when executed by at least one machine, causes the machine to:

emit at least one visible light stimulus by a display located on a front of a hardware device;

receive, from an infrared camera located on a front of a hardware device, image data corresponding to at least one eye of a user;

process the image data to identify at least one pupil feature; and determine a health status based on the at least one pupil feature.

10. The non-transitory machine-readable medium of embodiment 9, wherein the at least one pupil feature includes at least one of: pupil response latency, constriction latency, maximum constriction velocity, average constriction velocity, minimum pupil diameter, dilation velocity, 75% recovery time, average diameter, constriction amplitude, constriction percentage, pupil escape, baseline pupil amplitude, post-illumination pupil response, and any combination thereof.

11. The non-transitory machine-readable medium of embodiment 10, wherein the machine is further caused to emit a non-visible light comprising a light emission with a wavelength between 700 nm and 1000 nm.

Computer & Hardware Implementation of Disclosure

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

CONCLUSION

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

The invention claimed is:

1. A system for evaluating pupillary light reflex, the system comprising:
  a mobile device comprising a front and a back;
  a camera located on the front of the mobile device;
  a display located on the front of the mobile device;
  a processor; and
  a memory having stored therein machine-readable instructions executable by the processor, the processor configured to execute the machine-readable instructions to:
    receive, from the camera, first image data corresponding to at least one eye of a user when no light stimulus is provided by the display; and
    emit at least one visible light stimulus via the display by;
      determining an amount of luminous flux to provide based on the first image data;
      determining a portion of the display to output the determined amount of luminous flux based on the first image data; and
      emitting the determined amount of luminous flux on the determined portion of the display.

2. The system of claim 1, wherein the processor is further configured to:
  receive second image data of the at least one eye after outputting the luminous flux;
  process the second image data to identify at least one pupil feature;
  determine a health status based on the at least one pupil feature; and
  output the health status via the display.

3. The system of claim 2, wherein the camera is an infrared camera, and wherein the processor is further configured to:
  emit non-visible light by an infrared emitter, wherein the second image data is based on the visible light stimulus and the non-visible light.

4. The system of claim 2, wherein the at least one pupil feature includes at least one of: pupil response latency, constriction latency, maximum constriction velocity, average constriction velocity, minimum pupil diameter, dilation velocity, 75% recovery time, average pupil diameter, maximum pupil diameter, constriction amplitude, constriction percentage, pupil escape, baseline pupil amplitude, post-illumination pupil response, and any combination thereof.

5. The system of claim 2, wherein the health status determined based on the at least one pupil feature is further determined by:
  determining a difference between each of the at least one pupil feature and a corresponding healthy pupil measurement, wherein the corresponding healthy pupil measurement is retrieved, by the processor, from an external measurement database; and determining the health status based on the determined difference for each of the at least one pupil feature and the corresponding healthy pupil measurement.

6. The system of claim 2, wherein the processor is further configured to adjust the output luminous flux based on the second image data.

7. The system of claim 2, wherein the processor is further configured to:
  tag a first pupil response based on the received second image data;
  receive third image data;
  determine a change in lighting conditions based on the third image data; and
  tag a second pupil response.

8. The system of claim 1, wherein the at least one visible light stimulus comprises visible light only in the red, blue, or green spectrum.

9. A method for evaluating pupillary light reflex, the method comprising:
  receiving from an ambient light sensor, a set of lux data;
  comparing the set of lux data to a threshold;
  responsive to the set of lux data being below the threshold, initiating a display based pupillary light reflex application, the initiating of the display based pupillary light reflex application including:
    emitting at least one visible light stimulus via the display;
    emitting non-visible light via the display a predetermined time after emitting the at least one visible light stimulus;
    receiving, from a camera, image data corresponding to at least one eye of a user;
    processing the image data to identify at least one pupil feature; and
    determining a health status based on the at least one pupil feature.

10. The method of claim 9, further comprising providing a notification to a user to reduce the ambient lux if the set of lux data is above a threshold.

11. The method of claim 9, wherein the health status as determined based on the at least one pupil feature is abnormal aging of an eye of the user and the at least one visible light stimulus comprises light only in a green spectrum.

12. The method of claim 9, wherein the at least one pupil feature includes: pupil response latency, constriction latency, maximum constriction velocity, average constriction velocity, minimum pupil diameter, dilation velocity, 75% recovery time, average pupil diameter, maximum pupil diameter, constriction amplitude, constriction percentage, pupil escape, baseline pupil amplitude, post-illumination pupil response, or any combination thereof.

13. The method of claim 9, wherein the determining a health status based on the at least one pupil feature comprises:
  determining a difference between each of the at least one pupil feature and a corresponding healthy pupil measurement, wherein the corresponding healthy pupil measurement is retrieved, by the processor, from an external measurement database; and
  determining the health status based on the determined difference for each of the at least one pupil feature and the corresponding healthy pupil measurement.

14. The method of claim 9, wherein emitting at least one visible light stimulus by the display further comprises emitting visible light only in the red, blue, or green spectrum.

15. A system for evaluating pupillary light reflex, the system comprising:

a hardware device comprising a front and a back;

an infrared camera located on the front of the hardware device;

a display located on the front of the hardware device;

a processor; and a memory having stored therein machine-readable instructions executable by the processor, the processor configured to execute the machine-readable instructions to:

emit at least one visible light stimulus via the display;

emit non-visible light via the display;

receive, from the infrared camera, image data corresponding to at least one eye of a user;

process the image data to identify at least one pupil feature; and determine a health status based on the at least one pupil feature.

16. The system of claim 15, wherein the non-visible light comprises a light emission with a wavelength between 700 nm and 1,000 nm.

17. The system of claim 15, wherein the at least one pupil feature includes at least one of: pupil response latency, constriction latency, maximum constriction velocity, average constriction velocity, minimum pupil diameter, dilation velocity, 75% recovery time, average pupil diameter, maximum pupil diameter, constriction amplitude, constriction percentage, pupil escape, baseline pupil amplitude, post-illumination pupil response, and any combination thereof.

18. The system of claim 15, wherein the hardware device is one of a virtual reality headset or a mobile device.

* * * * *